United States Patent
Innes et al.

(10) Patent No.: US 9,678,052 B2
(45) Date of Patent: Jun. 13, 2017

(54) METHOD AND SYSTEM FOR TRACKING MATERIAL

(75) Inventors: Chris Innes, Baulkham Hills (AU); Eric Nettleton, Research (AU); Hugh Durrant-Whyte, Rozelle (AU); Arman Melkumyan, Lane Cove (AU)

(73) Assignee: The University of Sydney, The University of Sydney, New South Wales (AU)

( * ) Notice: Subject to any disclaimer, the term of this patent is extended or adjusted under 35 U.S.C. 154(b) by 811 days.

(21) Appl. No.: 13/824,313

(22) PCT Filed: Oct. 28, 2011

(86) PCT No.: PCT/AU2011/001389
§ 371 (c)(1),
(2), (4) Date: Jun. 5, 2013

(87) PCT Pub. No.: WO2012/054987
PCT Pub. Date: May 3, 2012

(65) Prior Publication Data
US 2013/0272829 A1    Oct. 17, 2013

(30) Foreign Application Priority Data
Oct. 29, 2010 (AU) ................ 2010904832

(51) Int. Cl.
*G06F 17/50* (2006.01)
*G01N 33/24* (2006.01)
(Continued)

(52) U.S. Cl.
CPC ............. *G01N 33/24* (2013.01); *B65G 67/04* (2013.01); *G01G 19/08* (2013.01)

(58) Field of Classification Search
USPC .................... 703/1; 702/82; 414/399; 299/8
See application file for complete search history.

(56) References Cited

U.S. PATENT DOCUMENTS

| 4,839,835 A | 6/1989 | Hagenbuch |
| 8,315,838 B2* | 11/2012 | Durrant-Whyte ...... G06Q 10/06 703/1 |
| 2004/0030426 A1 | 2/2004 | Popp et al. |

FOREIGN PATENT DOCUMENTS

WO    WO 2010/124339 A1    11/2010

OTHER PUBLICATIONS

PCT Notification of Transmittal of the International Search Report and the Written Opinion of the International Searching Authority, or the Declaration for PCT Counterpart Application No. PCT/AU2011/001389, 7 pgs., (Jan. 12, 2012).

(Continued)

*Primary Examiner* — Lam Nguyen
(74) *Attorney, Agent, or Firm* — Blakely, Sokoloff, Taylor & Zafman LLP

(57) ABSTRACT

Methods and systems are described for tracking material through a production chain or operational process chain in which the material is transferred via a plurality of spatially distinct lumped masses of material (12, 14, 16, 18). A dynamic state space (430) is maintained descriptive of the plurality of spatially distinct lumped masses of material, wherein a quantity of entries in the dynamic state space is augmented or diminished dependent on a quantity of spatially distinct lumped masses being tracked. Measurements relating to an observed lumped mass of material are fused into the dynamic state space and a dynamic covariance matrix to provide an updated estimate of material in the plurality of spatially distinct lumped masses of material.

37 Claims, 17 Drawing Sheets

(51) Int. Cl.
*G01G 19/08* (2006.01)
*B65G 67/04* (2006.01)

(56) References Cited

OTHER PUBLICATIONS

Elliot Duff, "Automated Volume Estimation of Haul-Truck Loads", Proceedings of the Australian Conference on Robotics and Automation, Melbourne, Australia, pp. 179-184, (2000).
N.J. Gordon, et al., "Novel Approach to Nonlinear/Non-Gaussian Bayesian State Estimation", IEE Proceedings-F on Radar and Signal Processing, vol. 140, No. 2, pp. 107-113, (Apr. 1993).
Stephen E. Cohn, "An Introduction to Estimation Theory", Journal of the Meteorological Society of Japan, vol. 75, No. 1B, pp. 257-288, (Mar. 1997).
Ottmar Bochardt, et al., "Generalized Information Representation and Compression Using Covariance Union", 9th International Conference on Information Fusion, pp. 1-7, (2006).

* cited by examiner

Initial

| | State Vector(x) | Covariance Matrix (P) | |
|---|---|---|---|
| Grade Block Mass | 4342 | 40 | 28 |
| Grade Block Vol | 3006 | 20 | 219 |

Predicted Excavator Ore Removal

| | | | | | | | |
|---|---|---|---|---|---|---|---|
| Grade Block Mass | 3994 | 1829 | 1266 | 0 | 0 | -1789 | -1239 |
| Grade Block Vol | 2765 | 1266 | 1077 | 0 | 0 | -1239 | -858 |
| Exv. Bucket Mass Loss | 0 | 0 | 0 | 0 | 0 | 0 | 0 |
| Exv. Bucket Vol Loss | 0 | 0 | 0 | 0 | 0 | 0 | 0 |
| Exv. Bucket Mass | 348 | -1789 | -1239 | 0 | 0 | 1789 | 1239 |
| Exv. Bucket Vol | 241 | -1239 | -858 | 0 | 0 | 1239 | 858 |

Excavator Observation Update

| | | | | | | | |
|---|---|---|---|---|---|---|---|
| Grade Block Mass | 3949 | 128 | 89 | 0 | 0 | -88 | -61 |
| Grade Block Vol | 2734 | 89 | 261 | 0 | 0 | -61 | -42 |
| Exv. Bucket Mass Loss | 0 | 0 | 0 | 0 | 0 | 0 | 0 |
| Exv. Bucket Vol Loss | 0 | 0 | 0 | 0 | 0 | 0 | 0 |
| Exv. Bucket Mass | 393 | -88 | -61 | 0 | 0 | 88 | 61 |
| Exv. Bucket Vol | 272 | -61 | -42 | 0 | 0 | 61 | 42 |

Figure 14

METHOD AND SYSTEM FOR TRACKING MATERIAL

CROSS-REFERENCE TO RELATED APPLICATIONS

This patent application is a U.S. National Phase Application under 35 U.S.C. §371 of International Application No. PCT/AU2011/001389, filed Oct. 28, 2011, entitled METHOD AND SYSTEM FOR TRACKING MATERIAL, which claims priority to Australian Patent Application No. 2010904832, filed Oct. 29, 2010.

FIELD OF THE INVENTION

The present invention relates to methods and systems for tracking lumped masses of material. In one application the invention relates to estimating and reconciling the properties of material through a mining system.

BACKGROUND OF THE INVENTION

The ability to accurately track bulk material properties through a production chain or operational process chain is highly valuable. In the mining industry, having incorrect estimates of grade and quantity in stockpiles can lead to financial penalties. Improving the quality of information by tracking material at each stage would enable mine engineers to perform greater planning to avoid these penalties.

An example of a production chain and an operational process chain is an open-pit iron-ore mine. In open-pit iron-ore mining, material is excavated from specific locations after being blasted. The amount excavated from each location is usually determined by production requirements to meet a certain level of quality and quantity of material. The excavated material is transported by haul trucks directly to dumping stations for primary crushing or to stockpiles, from which the material is removed for further processing. Material is also removed to enable the development of the pit to access future deposits. Such material is transported to dumping locations which may or may not be permanent. The material dumped may be used as fill for previous excavations.

One practice in mining is estimate material in haul trucks by assuming they carry a common constant percentage of their maximum load. This value, termed a 'load factor', is essentially the average mass of material moved by trucks calculated over a long timeline. This method, although accurate over large time frames, is prone to fluctuations based on operator skill through over/under filling of trucks and excavation of material outside of designated areas. It also relies upon the quality of initial in-ground estimates of the material being excavated.

There is an ongoing need for a probabilistically consistent framework for estimating the properties of excavated material as it progresses through a mining production chain, for example from the point of excavation to railing stockpiles and beyond.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In broad terms the methods described herein represent lumped masses of material probabilistically. A variety of sensors are used to measure different properties of the material at spatially distinct locations as the material is moved through a production chain or operational process chain. An appropriate framework for ensuring consistent data fusion is also described.

According to one aspect of the invention there is provided a method for tracking material through a production chain or operational process chain in which the material is transferred via a plurality of spatially distinct lumped masses of material, the method comprising:
  maintaining a dynamic state space descriptive of the plurality of spatially distinct lumped masses of material, wherein a quantity of entries in the dynamic state space is varied dependent on a quantity of spatially distinct lumped masses being tracked;
  maintaining a dynamic covariance matrix associated with the dynamic state space, wherein a dimension of the dynamic covariance matrix is varied dependent on a quantity of spatially distinct lumped masses of material being tracked;
  receiving one or more measurements relating to an observed lumped mass of material; and
  fusing the received one or more measurements into the dynamic state space and dynamic covariance matrix to provide an updated estimate of material in the plurality of spatially distinct lumped masses of material.

According to another aspect of the invention there is provided a system for tracking material through a mining production chain in which the material is transferred via a plurality of spatially distinct lumped masses of material, the system comprising:
  a plurality of sensors for measuring attributes of the spatially distinct lumped masses of material; and
  a processor in data communication with the plurality of sensors and comprising instructions that, in use, cause the processor to:
    maintain a dynamic state space descriptive of the plurality of spatially distinct lumped masses, wherein a quantity of entries in the dynamic state space is varied dependent on a quantity of spatially distinct lumped masses of material being tracked;
    receive one or more measurements from the plurality of sensors relating to an observed lumped mass of material; and
    fuse the received one or more measurements into the dynamic state space to provide an updated estimate of material in the plurality of spatially distinct lumped masses of material.

According to a further aspect of the invention there is provided a system for tracking material through a mining production chain, comprising:
  a) at least one excavator having:
    i) an excavator sensor that in use scans a surface of material to be excavated; and
    ii) a location sensor,
    wherein, based on the surface scan, an associated processor estimates a quantity of material excavated by the excavator as a first spatially distinct lumped mass of material;
  b) at least one haul truck that in use receives excavated material from the at least one excavator, wherein material loaded into the haul truck comprises a second spatially distinct lumped mass of material and wherein, in use, material is offloaded from the at least one haul truck to define at least a third spatially distinct lumped mass of material;

c) a monitoring system that tracks movement of the at least one haul truck; and d) a material-tracking processor in data communication with the at least one excavator, the at least one haul truck and the monitoring system, wherein the material tracking processor maintains a dynamic state space descriptive of the first, second and third spatially distinct lumped masses of material and fuses information characterising the material in the mining production chain to provide an updated estimate of the spatially distinct lumped masses of material.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS/FIGURES

Embodiments of the invention are described below with reference to the Figures, in which:

FIG. 14 shows a numerical example from the open pit mining operation to illustrate how the processing of fusing information at later stages improves estimates at earlier locations in the open pit mining operation.

DETAILED DESCRIPTION OF THE EMBODIMENTS

The tracking estimation methods described herein are described with reference to the example of an open pit mine, although the methods may also be applied in different applications.

Figure 1:
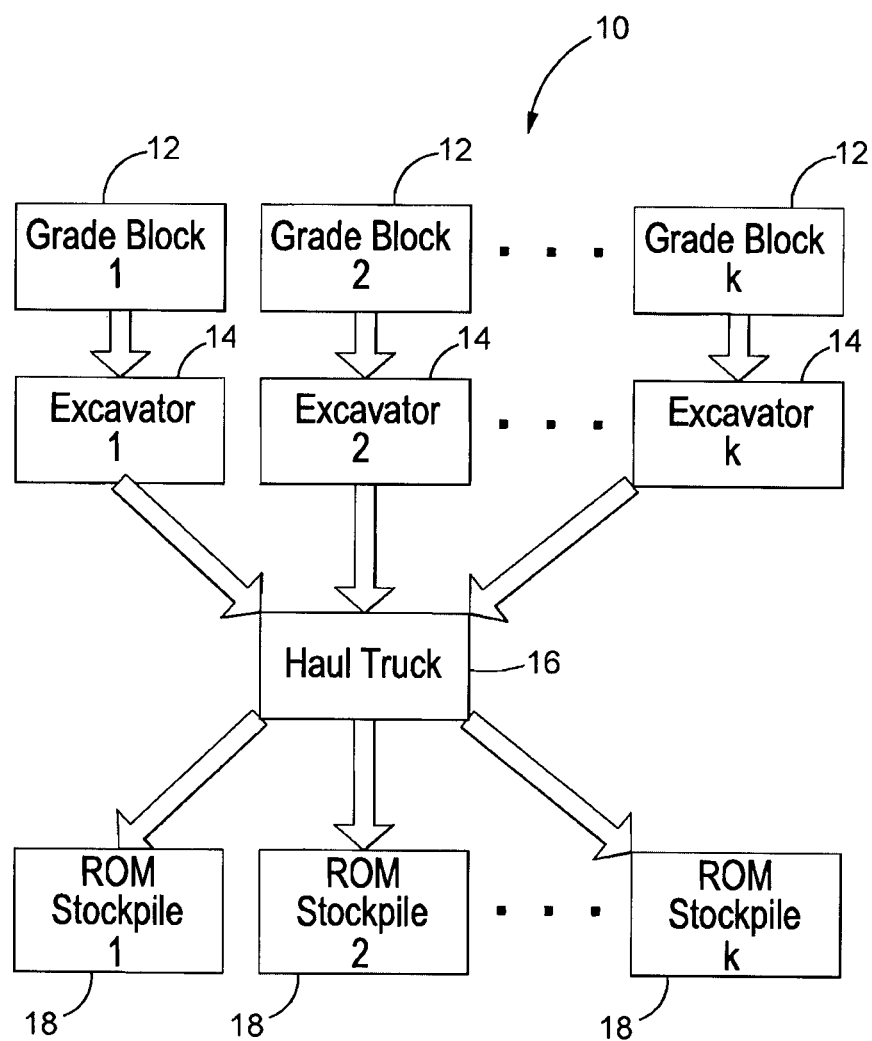
FIG. 1 is a schematic representation of a system in which material is excavated from a plurality of grade blocks and transported by haul trucks to a plurality of stockpiles.

FIG. 1 gives an example of an open pit production chain 10 in which material is tracked using the systematic approach outlined in this specification. A plurality of grade blocks 12 is excavated by a set of excavators 14. The material from the excavators 14 is loaded onto one or more haul trucks 16, which then unload the material at one or more locations such as run of mine (ROM) stockpiles 18 or a crusher.

Material in the production chain thus progresses through a series of spatially distinct lumped masses. Thus, material in grade block 1 is treated as a distinct lumped mass. Material removed from grade block 1 into the excavator bucket of excavator 1 is also treated as a distinct lumped mass, as is material loaded into a specific haul truck 16. Material in each of the ROM stockpiles 18 is also treated as a distinct lumped mass.

The illustrated production chain 10 extends from grade blocks 12 to ROM stockpiles 18. It will be appreciated that the production chain may extend further, for example via haulage from the ROM stockpiles to a rail network and on to stockpiles for a processing plant. Alternatively, the production chain may extend from a dump station through, primary and secondary crushers to stockpiles of processed material. The material may also go from the trucks straight to a crusher or plant without intermediate stockpiles. A tracking system is described below with reference to the example of FIG. 1, but the tracking methods may also be applied to other production chains.

Sensors

In order to track the lumped masses through the production chain, some information about the lumped masses is required. The equipment such as excavators 14 and haul trucks 16 may be provided with sensors that monitor one or more characteristics of the material. The characteristics include extensive properties such as mass and volume that define the amount of material in a lumped mass. The measured characteristics may also include intensive properties such as chemical composition or a fragmentation level of the material.

Sensor Technology—Mass

Excavator load cells and hydraulic pressures are currently two methods which are used in excavation industries and may be used in mining work to enable the estimation of mass inside excavator buckets. LoadMetrics™ is an example of a solution provided by Motion Metrics International Corp that offers pay load estimation of excavators.

Haul truck suspension-strut pressures currently on haul trucks may be input into the system to enable on-the-fly estimates of haul truck mass.

Sensor Technology—Volume

The calculation of bucket-fill volume information is currently available in solutions offered by Motion Metrics International Corp.

A commercially available system to calculate the volume of material in haul trucks is offered by Transcale Pty Ltd. (See E. Duff "Automated volume estimation of haul truck loads." Proceedings of the Australian Conference on Robotics and Automation, Melbourne, Australia: CSIRO, 2000 pp 179-184).

To determine volumes of stockpiles there is currently a plethora of options available that use data from surveying equipment. Observation of stockpile volumes may be done by an autonomous sensor vehicle with a surveying laser attached.

Sensor Technology—Location

The excavators 14 may include a mass sensor on the excavator bucket with GPS location of the end effector. On-board GPS of haul trucks 16 (e.g. from the Modular Mining dispatch system available from Modular Mining Systems Inc) may be used to determine where the material was unloaded.

In addition to the sensors located on mobile equipment units, there may be additional sensors in the production chain 10 that monitor the location and operation of the equipment units. For example, one or more cameras may record equipment movement.

Utilizing visual sensors in a mining environment is particularly challenging due to the large amounts of dust present on site. Sensors such as the mm Wave radar are useful in this domain due to their ability to penetrate through dust. Some of the systems currently used in observation of material at various stages in the mining processes include autonomous estimation of haul truck contents (e.g. Mass, Volume). Use of hyperspectral cameras may also be used to determine intensive material properties at different stages of the mining process.

Figure 2A:
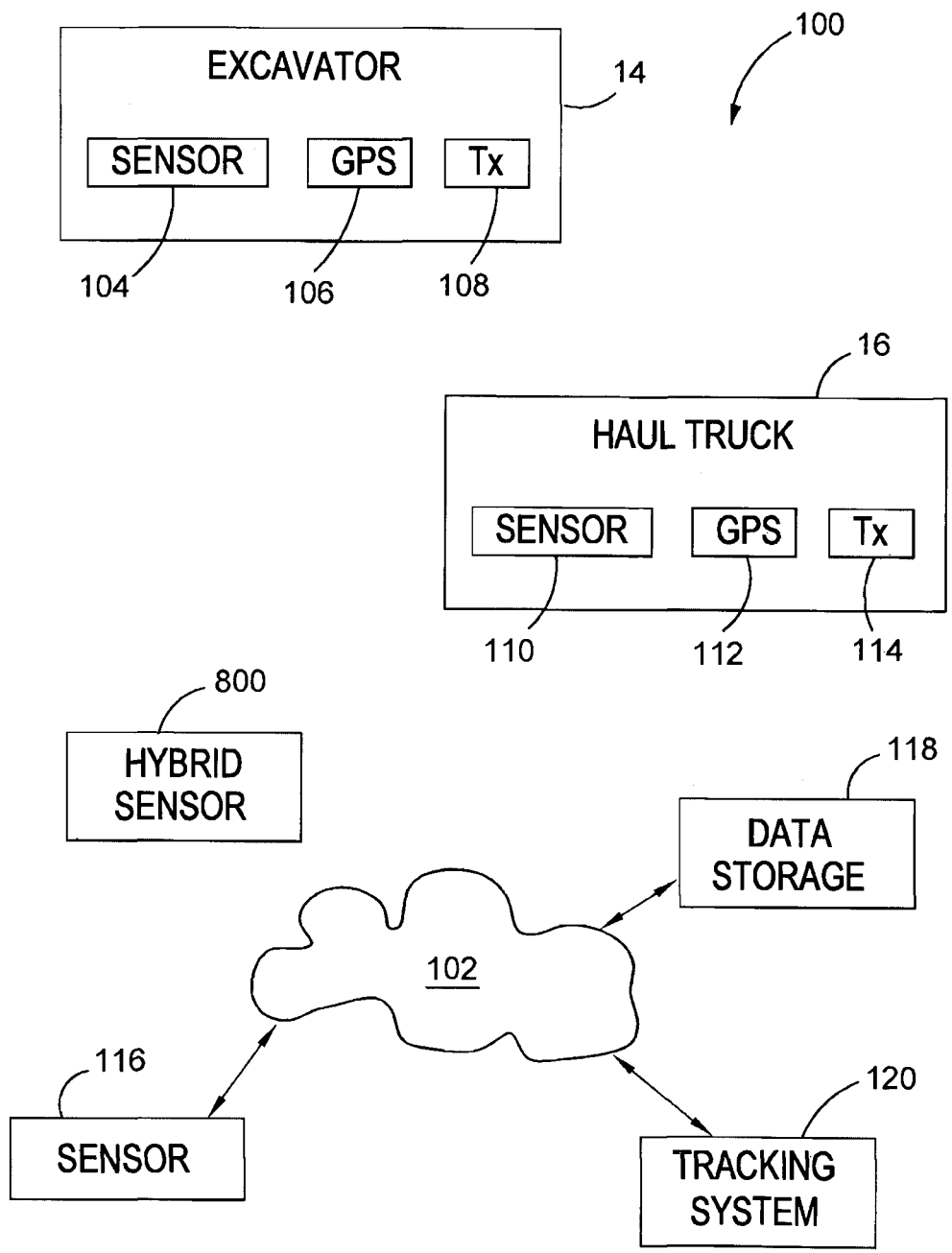
FIG. 2A is a schematic representation of a system in which the tracking methods described herein may be implemented.
Figure 2B:
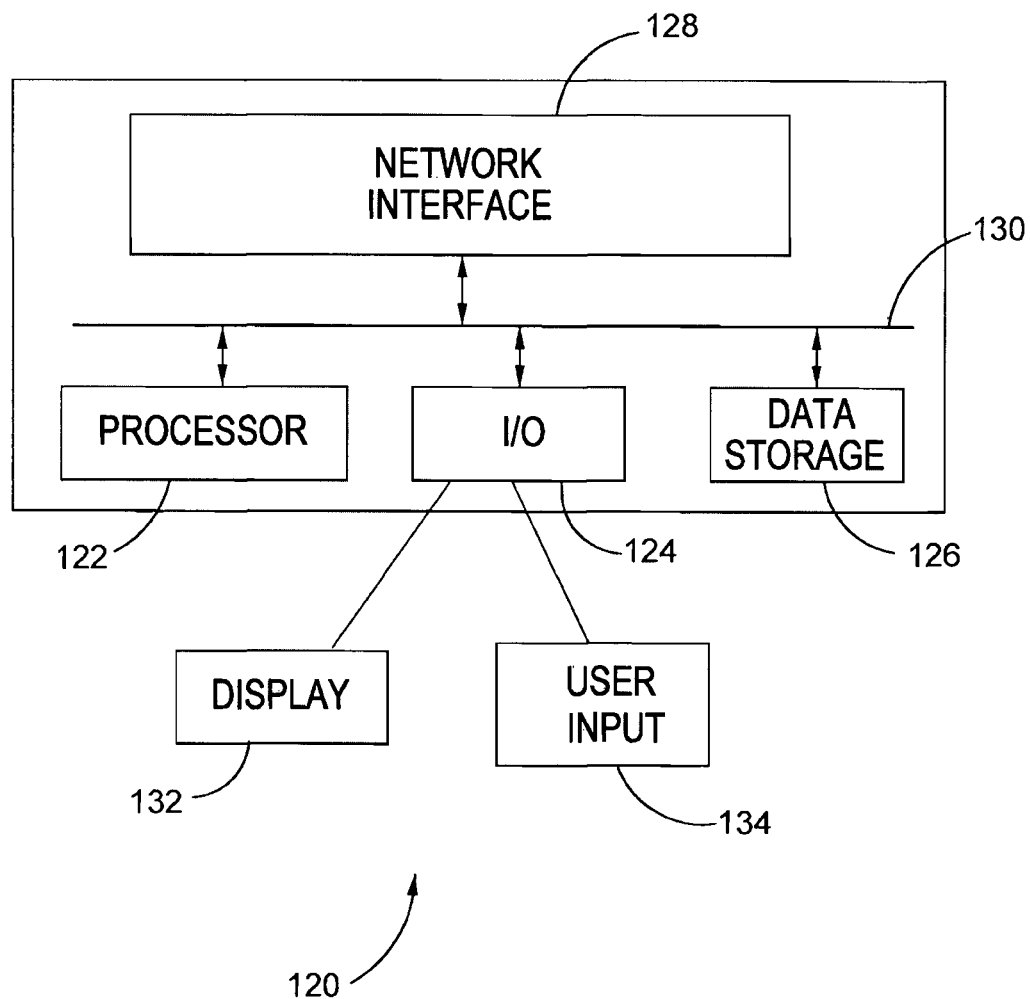
FIG. 2B is a schematic representation of a computing device on which the described methods may be implemented in the system of FIG. 2A.
Figure 2C:
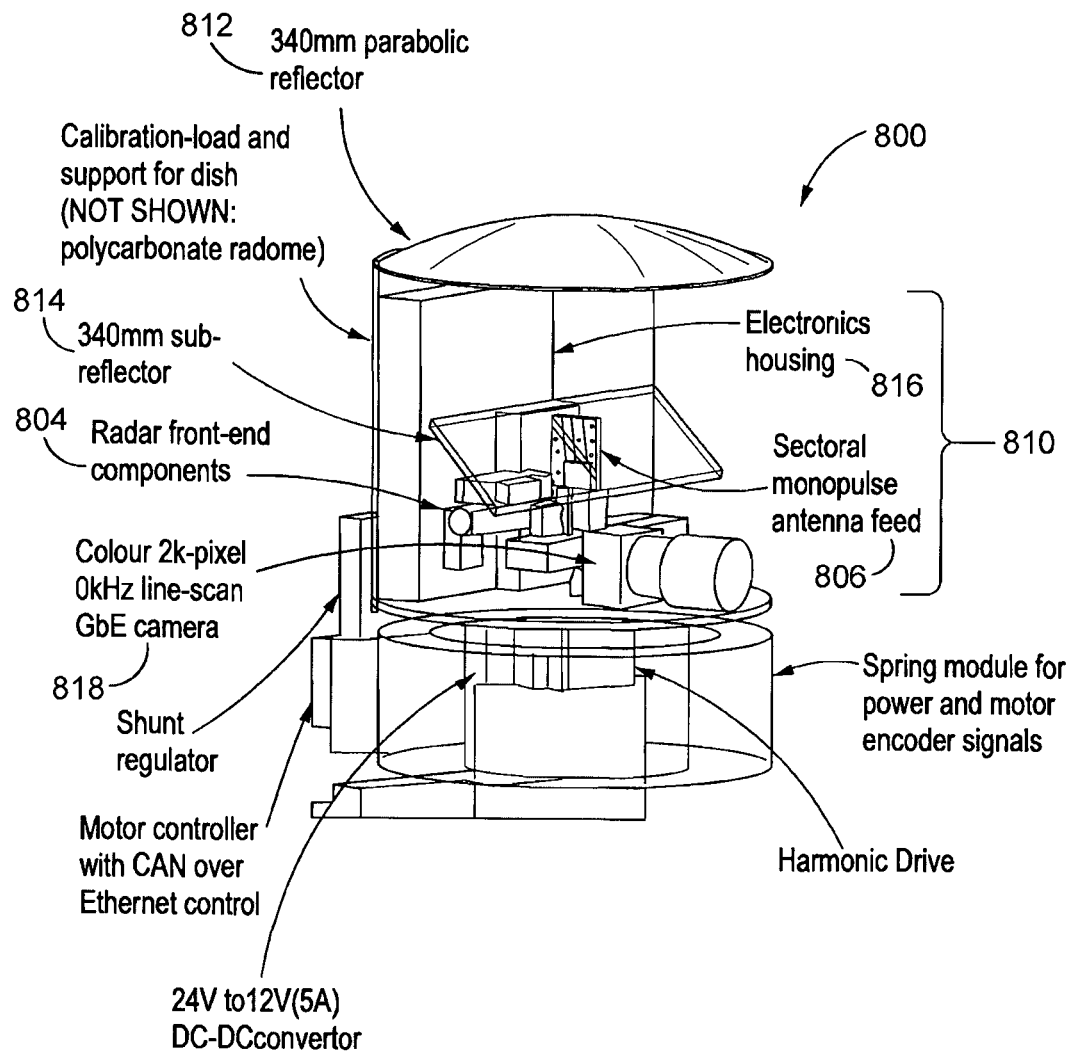
FIG. 2C shows a hybrid sensor that includes a radar system and a camera.

FIG. 2C shows an example of a hybrid sensor 800 including a radar system and a camera that are used to scan the terrain. The hybrid sensor 800 may, for example, be mounted on a vehicle that moves through the terrain to be scanned. The radar has a transmitter 806 and two receivers mounted vertically at the centre of a rotating section 810 (with the transmitter 806 in the middle). The transmitted beam travels vertically and spreads to cover a large proportion of the parabolic dish 812 where the beam is collimated and reflected back down onto the large sub-reflector 814 (mounted at an angle of 48.5°). The sub-reflector reflects the radar beam outwards with an azimuth beamwidth of 0.7° and an elevation beamwidth of 5°.

The sensor 800 also includes a camera 818. In one arrangement the camera has an update rate of up to 9.2 kHz (per line) and a system scan rate of 2 Hz. A 50 mm focal-length lens gives around 30° field-of-view in elevation, providing data that may be tied to the radar returns, as well as close-range and above-ground target information, in the form of one 10 Mpixel panoramic image per revolution.

A rotating section 810 (which includes the FPGA-based electronics in housing 816, radar front-end 804 and camera 818), rotates at a rate of 2 revolutions-per-second (RPS), gathering 2000 range profiles per revolution. The rotating section has a harmonic-drive hollow core motor to drive the rotation. The motor controller may be linked to a Control Area Network (CAN) over a gigabit Ethernet (GbE) link, which may be wireless.

Data from the sensor 800 may be communicated over the network to a host computer for example tracking system 120 described with reference to FIG. 2B. The host computer may have direct control over the scanning motor and line-scan camera 818. The host computer may also communicate with an embedded processor in the hybrid sensor 800 to pass control instructions and receive pre-processed data such as range profiles for each channel after each chirp. 3-D geometric information may be formed by software running on the host computer using time-stamped data from the radar and camera of the hybrid sensor.

Sensor Technology—Chemical

Chemical data on material once out of ground may be obtained in several ways. It is possible to use hyper-spectral cameras to get an estimate of chemical properties on the visible face of material.

Information may also be available about the quantity and stocks of in-ground material, including chemical and mechanical properties of different zones of a mine. For example, an in-ground model may provide a description of the disposition of shale, Banded Iron Formation (BIF) and iron ore zones, chemical composition and mechanical properties of these zones including rock factors and hardness. Sources for the in-ground modelling include surveys, rock recognition systems, chemical assays and exploration holes.

Sensor Technology—Fragmentation

Fragmentation levels of material may be obtained in haul truck scanning, for example using the CSIRO solution described in the Duff reference cited above.

Sensor Network Requirements

Preferably the system obtains the most accurate estimates by having a dense sensor network observing the system at each location. Realistically though, this is likely to be limited due to technical and practical considerations.

FIG. 2A shows a schematic view of a system 100 on which the tracking methods described herein may be implemented. The system includes one or more excavators 14, each excavator having one or more sensors 104. The sensors may measure mass or volume. The excavators typically also include a Global Positioning System 106 that monitors the location of the excavator. A transmitter is provided so that data from the sensors 104 and GPS 106 may be communicated through the system 100. Typically the excavator has a communications receiver to receive data and commands from other elements of the system 100.

The system also includes one or more haul trucks 16, each truck having one or more sensors 110. The sensors may measure mass or volume of material in the truck: The haul trucks typically also include a Global Positioning System 112 that monitors the location of the truck. A transmitter is provided so that data from the sensors 110 and GPS 112 may be communicated through the system 100. Typically the haul truck has a communications receiver to receive data and commands from other elements of the system 100.

The excavators 14 and trucks 16 may in some applications be autonomous vehicles. The system 100 may also include other mobile equipment that generates data relevant to the tracking methods described below. For example, mobile face-scanners may move through the open pit mine, providing information about material to be excavated. For example, a hyper-spectral sensor may provide measurements of the composition of material in a scanned surface. There may also be non-mobile sensors, for example a camera system that monitors movement of vehicles such as the excavators 14 and trucks 16. The terrain may be scanned using the hybrid scanner 800 described above with reference to FIG. 2C.

In system 100 the data generated by the sensors 104; 106, 110, 112, 116, 800 is disseminated via a network 102, which may be any suitable communications network, for example an intranet or the Internet. One or more data storage systems 118 is generally connected to the network 102. The data storage may include in-ground models of the open pit mine, including terrain modelling and geological models of the material in the pit.

A tracking system 120 is in data communication with the network 102. In one arrangement the tracking system may be a general-purpose computer as described with reference to FIG. 2B. The tracking system 120 includes at least one processor 122 and data storage 126, which may include semiconductor random access memory (RAM) and read only memory (ROM). Data storage in the tracking system may also include a hard-disk drive and non-volatile sources of data such as CD-ROM or DVD.

The tracking system 120 typically includes input/output (I/O) drivers to provide access to user inputs 134 such as a keyboard and mouse and outputs such as a display 132. Speakers may also output audio information. A network interface system 128 provides access to the network 102.

The components of the tracking system 120 typically communicate via a bus 130. The methods described below may be implemented via software instructions that are executed by the tracking system 120. The software may be stored in a computer readable medium and loaded onto the tracking system 120. A computer readable medium having software recorded on it is a computer program product.

The tracking methods described below may also be implemented in customised hardware within system 100, for example using one or more Digital Signal Processors (DSPs), Field Programmable Gate Arrays (FPGAs) or Application Specific Integrated Circuits (ASICs).

The tracking methods may also be implemented in a distributed fashion rather than as software running on a single unit 120. Alternatively, the tracking methods may also be incorporated into a broader mining automation system, for example the integrated automation system described in PCT application PCT/AU2010/000498, "Integrated automation system with picture compilation system", filed on 30 Apr. 2010, the contents of which are incorporated by cross-reference.

Autonomous Bulk Volume Estimation

One application for a lumped mass tracking system is implementation in an autonomous environment (specifically autonomous mining). Data fused into the system may also be gathered autonomously, for example from sensors 104, 106, 110, 112 mounted on mobile autonomous vehicles. A method for autonomously estimating a volume of material from a sensor scan of surfaces of the material is now described. A surface scan can be produced from a variety of sensors (radar, camera, laser). A suitable sensor in the mining domain would be a mm-wave radar, given its dust penetration properties. In other tests, the source of the surface scan may be a laser, specifically a Riegl LMSZ-620 3-d Surveying Laser.

The estimation may be achieved by using a formulation based on Gaussian processes (GPs). The estimation may be performed by a local processor, for example a processor located on an excavator 14 or other mobile device. The estimation may also be performed at a remote processor, such as tracking system 120.

We have for a Gaussian Process $$\begin{bmatrix} y \\ f_* \end{bmatrix} \sim N\left(0, \begin{bmatrix} K(X,X)+\sigma_n^2 I & K(X,X_*) \\ K(X_*,X) & K(X_*,X_*) \end{bmatrix}\right) \text{ and}$$

$$E(f_*) = K(X_*,X)[K(X,X)+\sigma_n^2 I]^{-1} y$$

$$\text{cov}(f_*) = K(X_*,X_*) - K(X_*,X)[K(X,X)+\sigma_n^2 I]^{-1} K(X,X_*)$$

In the case of a single point x* these equations become $$E[f_*(x_*)] = K(x_*,X)[K(X,X)+\sigma_n^2 I]^{-1} y$$

$$\text{var}[f_*(x_*)] = K(x_*,x_*) - K(x_*,X)[K(X,X)+\sigma_n^2 I]^{-1} K(X,x_*)$$

For the volume $$V = \int_S f_*(u) du$$

where S is the region of integration, the mean and variance can be expressed in the following forms:

$$E[V] = \int_S E[f_*(u)] du = (\int_S K(u,X) du)[K(X,X)+\sigma_n^2 I]^{-1} y$$

$$\begin{aligned} \text{var}[V] &= E[(V - E(V))^2] \\ &= E\left[\left(\int_S f_*(u)du - \int_S E[f_*(u)]du\right)^2\right] \\ &= E\left[\left(\int_S (f_*(u) - E[f_*(u)])du\right)^2\right] \\ &= E\left[\left(\int_S (f_*(u) - E[f_*(u)])du\right)\left(\int_S (f_*(w) - E[f_*(w)])dw\right)\right] \\ &= E\left[\int_S \int_S (f_*(u) - E[f_*(u)])(f_*(w) - E[f_*(w)])du\,dw\right] \\ &= \int_S \int_S E[(f_*(u) - E[f_*(u)])(f_*(w) - E[f_*(w)])]du\,dw \\ &= \int_S \int_S \text{cov}(f_*(u), f_*(w))du\,dw \end{aligned}$$

where K(x,x') is the covariance function of the GP representing the function f(x).

Effectively, the mean volume is calculated as a triple integral of the resultant points estimated by the Gaussian process.
i.e.

$$\iiint \hat{x}, \hat{y}, \hat{z}\, dx\, dy\, dz$$

The covariance function used is the squared exponential function, which is suitable for this particular application given its infinitely differentiable property. Because of this, it naturally creates smooth curves on the output function. The surfaces to estimate in iron ore mining are generally smooth. The inputs into the gaussian process are:
Training Set:

$$X = \begin{bmatrix} \bar{x} \\ \bar{y} \end{bmatrix}, y = \bar{z}$$

Given that the purpose of this algorithm is to calculate absolute volume, it may be necessary to shift the initial training data on the Z plane to ensure all positive z values.

$$\bar{z} = \bar{z} + \min(\bar{z})$$

Test Points:

$$X_* = \begin{bmatrix} \hat{x} \\ \hat{y} \end{bmatrix}$$

The result from the GP is:
z, which is equal to the predicted mean of the output function at (x,y) and
var[z], the predicted variance on z.

By being able to designate x-y co-ordinates to estimate on the surface, calculating the triple integral becomes tractable. This is possible due to separable integrals. Therefore one can do 2-d iterations (x-z or y-z as the point locations can be conveniently defined for integration) then iteratively integrating over the 3rd dimension (x or y).

Figure 3:
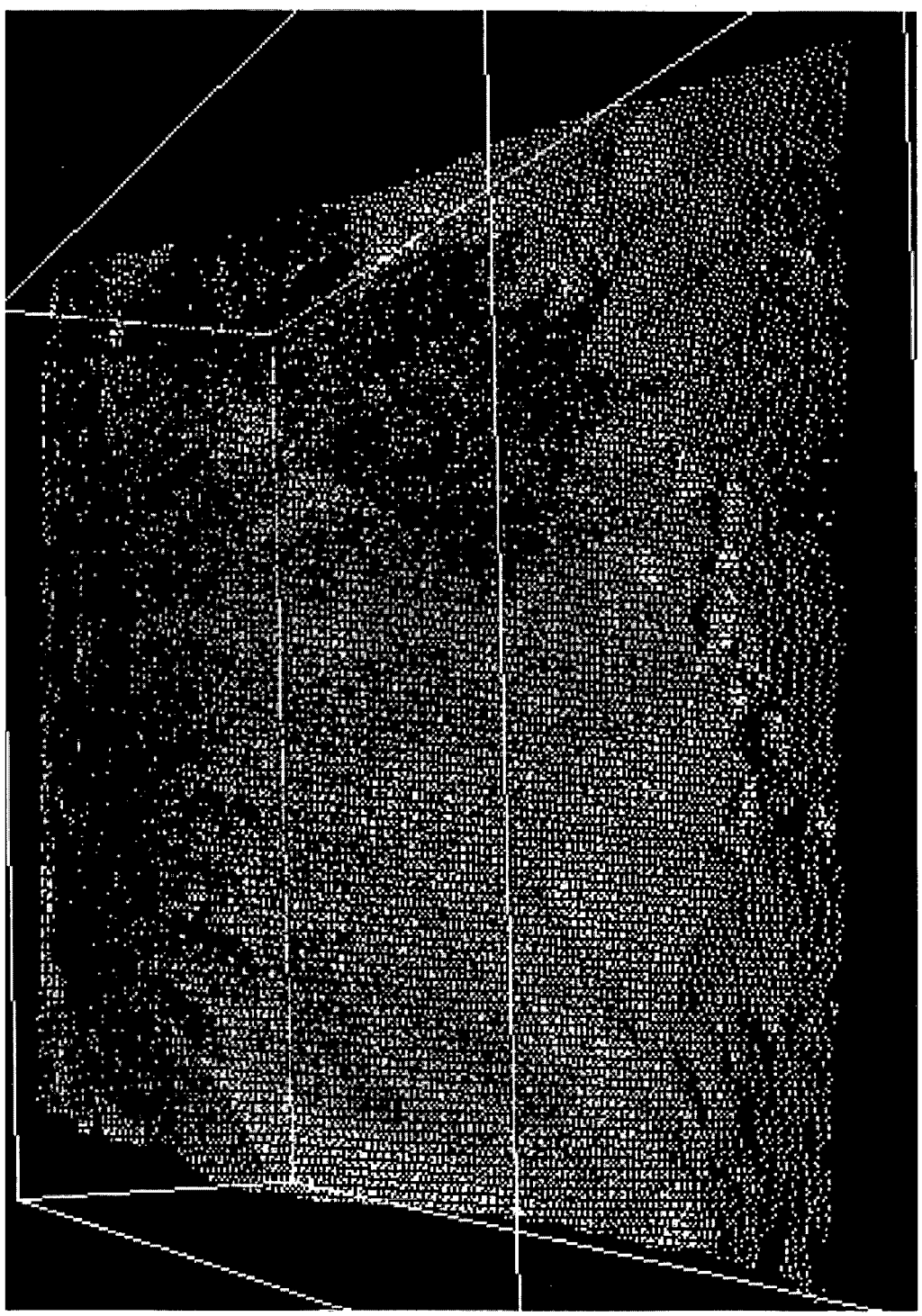
FIG. 3 shows raw data from a scan of a stockpile.
Figure 4:
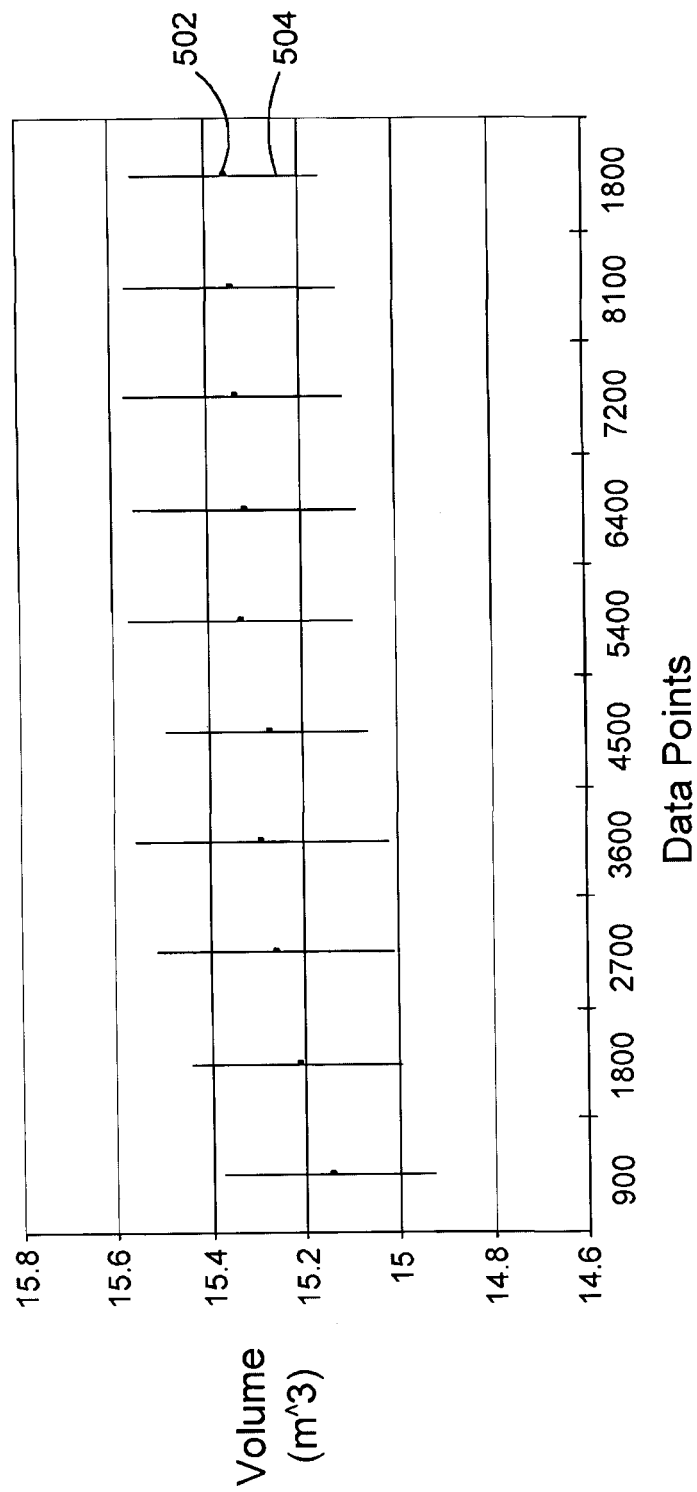
FIG. 4 shows volume estimates obtained using different quantities of data points from the raw data of FIG. 3.
Figure 5:
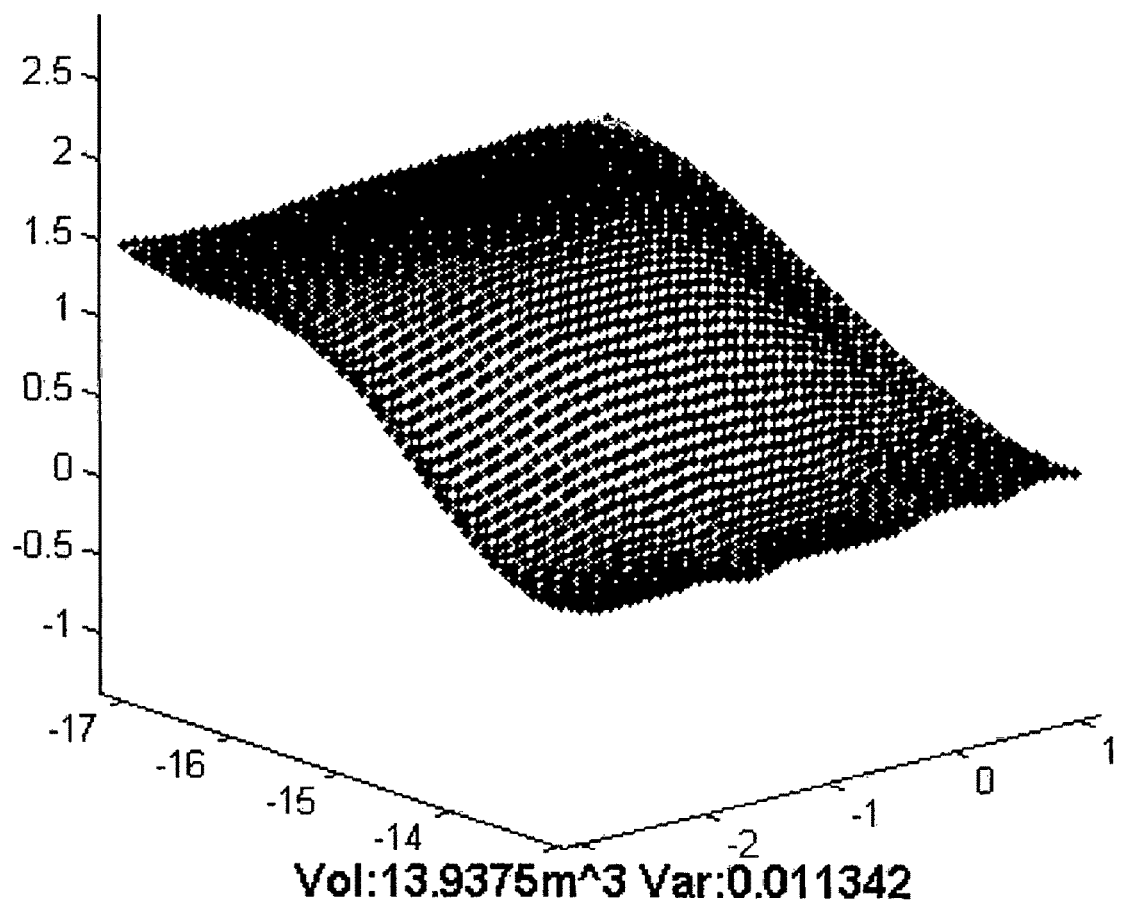
FIG. 5 shows the output of a volume estimate of the stockpile based on the application of a Gaussian process (GP) to the data of FIG. 3.

FIG. 3 shows an example of raw data from the Riegl Scanner of a stockpile. FIGS. 4 and 5 show the result of applying the above technique. The variance shown in FIG. 4 is a result of the variance from the Gaussian process plus an additional variance based on the variability in data points randomly chosen from the initial data set.

The raw data in this example has approximately 64000 data points in total. The Gaussian process uses 3600 of those points to produce FIG. 5. The variance on the result based on test data selection was calculated using an iterative approach. Some of the results can be seen in FIG. 4, which shows a set of volume estimates (eg 502). A line (eg 504) is shown for each estimate that indicates two standard deviations around the estimate. Each volume estimate is obtained based on a different quantity of data points from the raw data. For example, estimate 502 is based on 9000 data points.

Figure 6:
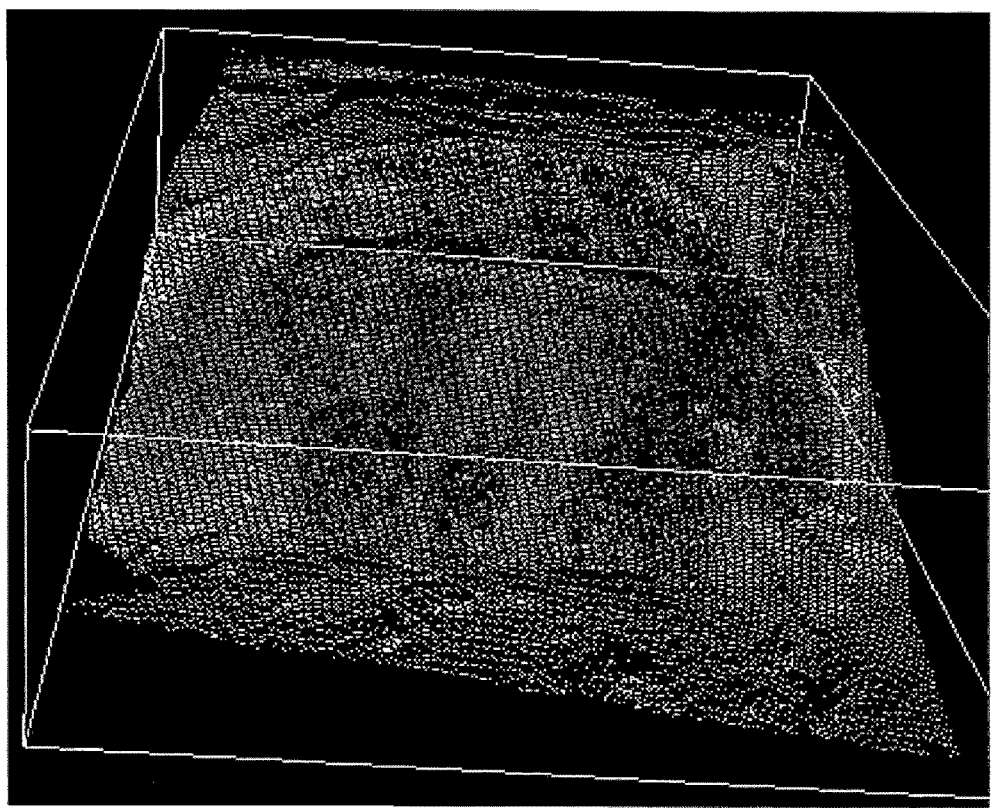
FIG. 6 shows raw data of the stockpile of FIG. 3 after a bucket load is removed.
Figure 7:
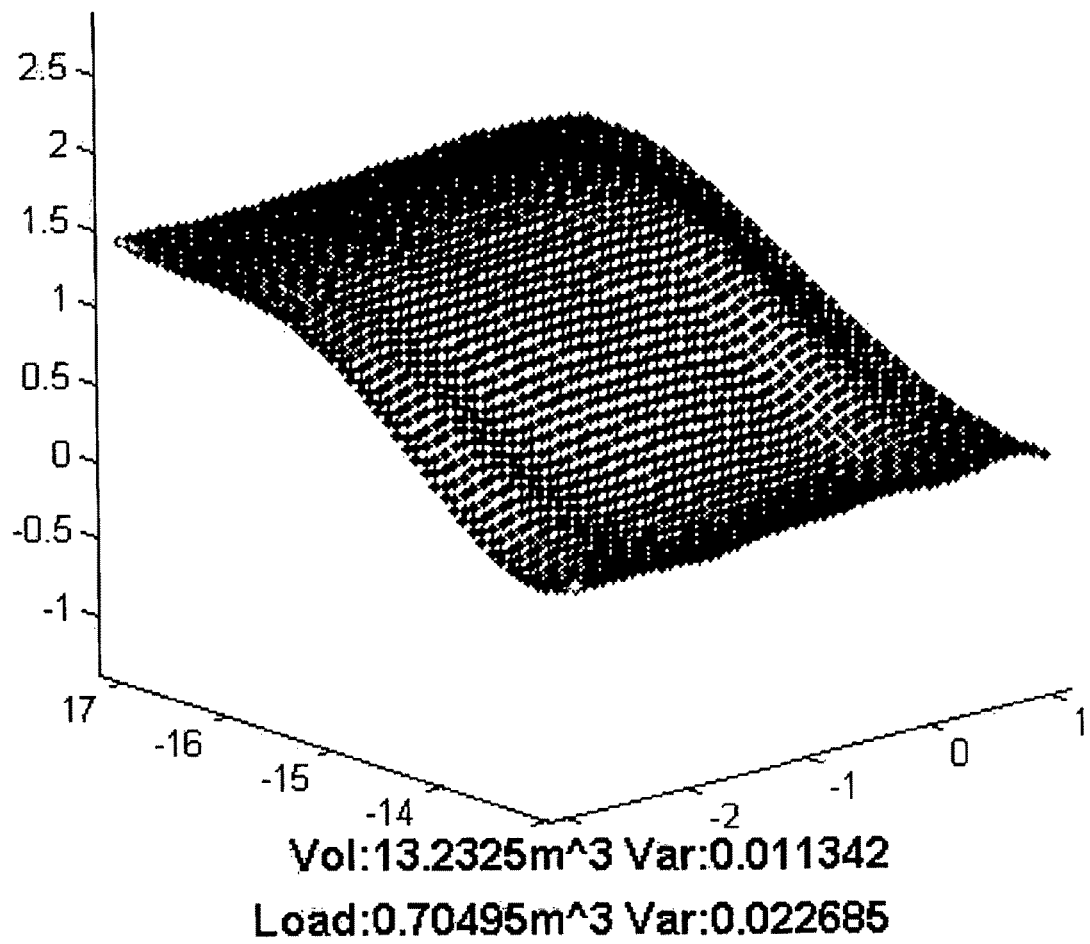
FIG. 7 shows the GP applied to the raw data of FIG. 6 to obtain a volume estimate.

This technique is useful in mining as it is possible to estimate from two successive scans of an excavation face how much material was removed in each bucket load. As an example, 1 bucket load is removed from the stockpile shown in FIG. 3. The resultant raw scan can be seen in FIG. 6. By subtracting the mean volume estimates and adding the variances from each scan, an estimate of the amount of material removed can be made. This can be seen in the result shown in FIG. 7.

Lumped Mass Model

The lumped mass model used in the tracking system 120 is a representation for discretising the excavated material into manageable components based on their physical location. This is done to reduce the complexity of the estimation problem into smaller manageable problems. The lumped mass model implies that material is estimated based on its physical separation from other lumped masses of material.

For example, material located in an excavator bucket is physically separated from both the material remaining in the grade block and the material in the haul truck. The spatially distinct materials are estimated separately. When the excavator bucket unloads into the haul truck, the material is merged with the material in the haul truck to create a new lumped mass which is estimated. The excavator bucket lumped mass is then no longer estimated since there is no material at that location until the excavator bucket again excavates more material.

Multiple information sources are fused together to provide a consistent estimate for excavated material. The lumped mass model may use the following representation:

$$P(X_n) \quad (1)$$

Where $$X_n = [M, V, Fc, SiO_2, Al_2O_3, Origin]^T \quad (2)$$

$X_n$ is a vector of material properties to be estimated. For the described example iron ore properties will be used. This equation simply states that at each spatially distinct lumped mass location a probabilistic representation will exist for each of the listed material properties defined in the vector Xn, where n represents the location identifier for each lumped mass (e.g. Excavator Bucket, Haul Truck, Stockpile).

The properties may include:
M=Mass
V=Volume
Fe=Iron %
$SiO_2$=Silicon Dioxide %
$Al_2O_3$=Aluminium Oxide %
Fragmentation=Ore Fragmentation Level
Origin=Co-ordinates of where original material was located in-situ.

Mass may be used as the measure in estimating other intensive material properties when combining lumped masses of material. An alternative selection would be to use the volume of material present in lumped masses. Mass and volume represent two extensive qualities of lumped material which can measure the quantity of the material present at any location. Typically however, mass is a more readily measurable quantity compared to volume. The majority of volume estimation techniques use a 3D point cloud of the surface (provided by an external sensor), which then can be used to either triangulate to create a surface projected against a plane, or through a point-axis integration method to determine a volume of material under this surface. This volume calculated is the bulk volume. Bulk volume is the volume of area the material occupies including the gap spaces between lumped material. Volume can be extrapolated from this by determination of the bulk factor.

$$B_f = \frac{V_b}{V_t}$$

Where: $B_f$=Bulk Factor
$V_b$=Bulk Volume
$V_t$=Volume

Depending on the consistency of the material and the configuration in the space which it is occupying, this can lead to variations on the bulk factor. Because of this difficulty in measuring volume explicitly, it is more appropriate to use mass as it can be relatively easier to measure by a range of sensors.

Data Fusion Engine

The Kalman filter is a state estimation method that may be used to fuse additional information provided about the lumped masses of material at different locations. Alternative embodiments may use a different estimator, such as a particle filter for example. Further information about particle filters may be found, for example, in:

Ristic, B.; Arulampalam, S.; Gordon, N. (2004). *Beyond the Kalman Filter: Particle Filters for Tracking Applications*. Artech House, and Gordon, N. J.; Salmond, D. J. and Smith, A. F. M. (1993). "Novel approach to nonlinear/non-Gaussian Bayesian state estimation". IEE Proceedings—F on Radar and Signal Processing, 140 (2): 107-113.

The Kalman filter follows a recursive 2 step process. The initial step is generally called the 'prediction step', where system models are used to project value of estimated states ahead in time. Lumped material modelling is a process-based system (the states to estimate change through processes such as the operation of an excavator, rather than time). So in effect the 'prediction step' is used in predicting how states change based on the effect of a process on those states. Equations 3 and 4 show this 'prediction step'. In Equation 3 $u_k$ (linear control input) and $q_k$ (system noise) will be assumed to be 0. F is known as the state-transition matrix, and describes how the states in vector $X_k$ will change after a given process. $P_k$ is the covariance matrix describing how the different states relate to each other. $Q_k$ and G denote respectively system noise and a projection matrix of that noise onto estimated states.

Prediction Step:

$$x_{k+1} = Fx_k + Bu_k + Gq_k \quad (3)$$

$$P_{k+1} = FP_k F' G Q_k G' \quad (4)$$

The process after prediction is known as the 'update step'. The update step consists of an independent sensor observation of one or more of the states and the fusion of this information into the current state vector and covariance matrix.

Update Step:

$$v_{k+1} = z_{k+1} - Hx_{k+1} \quad (5)$$

$$S_{k+1} = HPH' + R \quad (6)$$

$$W_{k+1} = P_{k+1} H (S_{k+1})^{-1} \quad (7)$$

$$x_{k+1}^+ = x_{k+1}^- + W_{k+1} v \quad (8)$$

$$P_{k+1}^+ = P_{k+1}^- - W_{k+1} S_{k+1} W'_{k+1} \quad (9)$$

where, z=State Observation Vector. H Describes how observation space maps to state space. R=Sensor Noise. v=Innovation (Error between observed states and corresponding predicted states). S=Innovation Covariance and W=Kalman Weighting which describes how much weight to apply to the sensor observation compared to the original estimate on affected states.

Figure 8A:
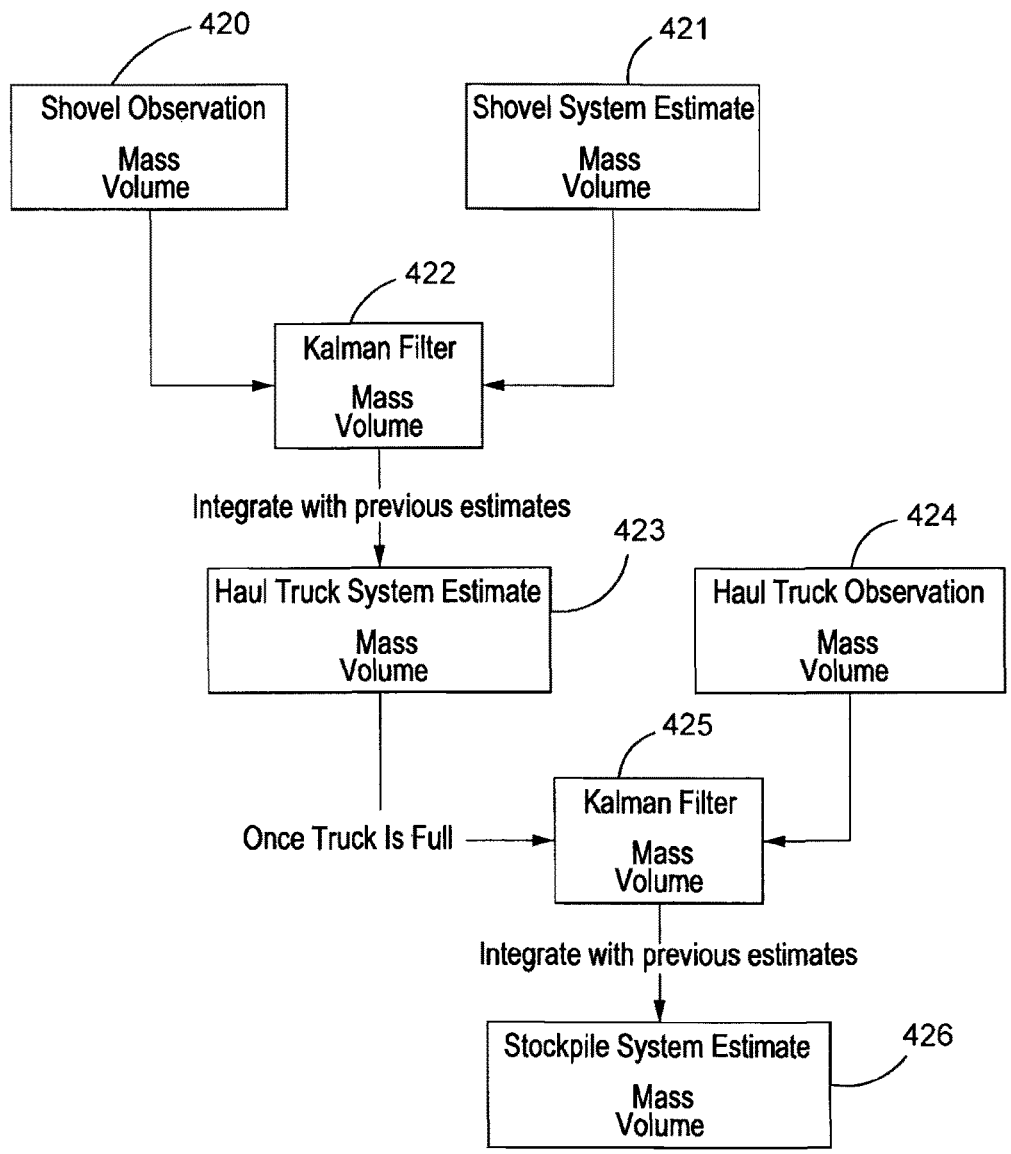
FIG. 8A is a schematic representation of an estimation system using multiple Kalman filters to track material from a shovel via a haul truck to a stockpile.

When choosing to model the amount of material at each location a simple solution is to dedicate a Kalman filter for each location. This choice would be beneficial in that computationally the system is always tractable due to the small size of the covariance matrix (Size equivalent to $X_n^2$). Computational speed is a necessity in any system which has the intention of being operated in a real-time environment. FIG. 8A is an example of how multiple Kalman filters may be used in the mining application. A shovel observation 420 of mass and volume, together with a shovel system estimate 421, is provided to Kalman filter 422, which integrates the observation with previous estimates and provides the updated estimate to a haul truck estimate 423. Kalman filter 425 uses the estimate 423 together with haul truck observations 424 to update the haul truck estimate and provides the update to a stockpile system estimate 426. The multiple Kalman filters 422, 425 may be implemented as software running on distributed processors, or at a central location such as tracking system 120.

The multiple instances of separate Kalman filters have a drawback in practice. Lumped material estimates of material separated from other lumped materials are correlated to those original lumped material estimates. This correlation may be crucial in ensuring system mass consistency and reconciliation. This correlation is not inherently maintained in a multiple instance Kalman filter approach.

To maintain the correlations in the system, an 'Augmented State Kalman Filter' may be used. In this approach a deviation from the Kalman filtering of FIG. 8A is that the system has a state vector which is dynamic, in the sense that the state vector expands and decreases as the amount of physically unique lumped masses of material in the system evolves over time. Mathematically, this can be seen in Equation 10.

$$X_s = [X_1, X_2, \ldots, X_{j-1}, X_j]^T \quad (10)$$

$X_s$ is a vector space with j vectors. The vector $X_i \in X_S$, where $i=[1, 2 \ldots, j-1, j]$, represents a spatially distinct lumped mass. $X_i$ contains states such as those shown in Equation 2. $X_s$ effectively therefore contains all states to be measured in the system. Given this information $X_s$ can be seen as the equivalent to the state vector $X_k$ commonly given in Kalman filtering literature.

Figure 8B:
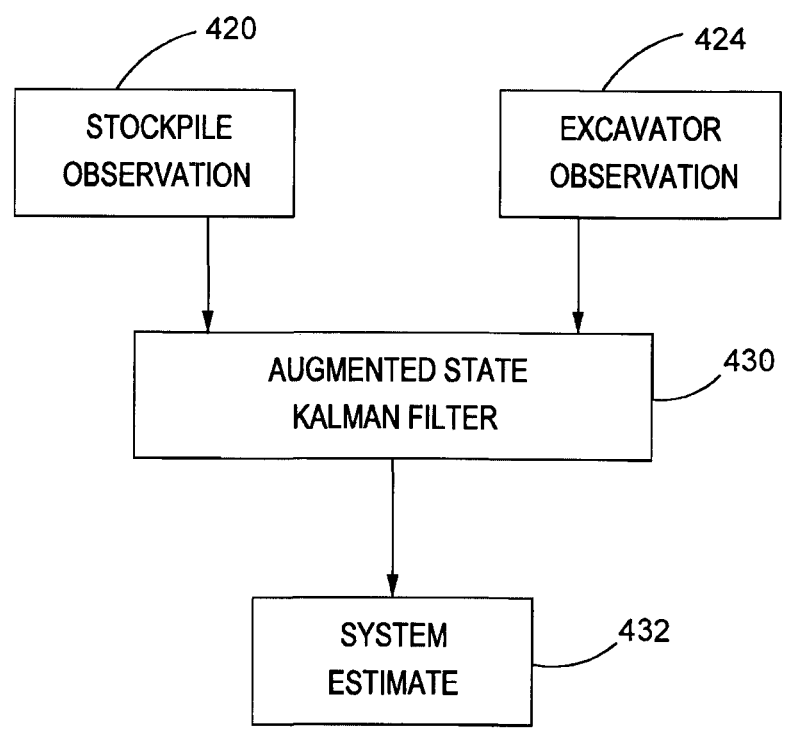
FIG. 8B is a schematic representation of an estimation system using an augmented state Kalman filter.

An example of a system with a dynamic augmented state Kalman filter is shown in FIG. 8B. The process involves a stockpile from which an excavator removes material. Excavator observations 424 and stockpile observations 420 are provided as inputs to an augmented state Kalman filter 430, which provides a system estimate 432.

Initializing and Removing Lumped Mass States

Initializing and removing new lumped mass vectors ($X_n$) into the system is described below. Equations 11-14 explain the process of initializing a new state:

$$x_{k,x_n} = \begin{bmatrix} x_k \\ X_n \end{bmatrix} \quad (11)$$

$$P_{k,x_n} = \begin{bmatrix} P_k & 0 \\ 0 & \sigma_{X_n}^2 \end{bmatrix} \quad (12)$$

$$x_k^\# = A x_{k,x_n} \quad (13)$$

$$P_k^\# = A P_{k,x_n} A^T + B Q_{k,x_n} B^T \quad (14)$$

where A and B are design matrices used to initialize the new states models, system models and correlations to previous states in the state vector and covariance matrix.

$x_k^\#$=the state vector post initialization of the new lumped mass. $P_k^\#$=the covariance matrix post initialization.

A very simple example is a filter with one existing lumped mass. For this example the existing lumped mass is a stockpile from which an excavator will remove material. The only property to estimate is mass ($X_n$=[m]). Assuming that the prediction model noise is zero, the equations below describe the loading process and the development of the correlations between the two lumped mass states. Variables:

$$x_{k,x_n} = \begin{bmatrix} m_{stockpile} \\ m_{excavator} \end{bmatrix} \quad (15)$$

$$A = \begin{bmatrix} 1 & -1 \\ 0 & 1 \end{bmatrix} \quad (16)$$

$$B = \begin{bmatrix} 1 & -1 \\ 0 & 1 \end{bmatrix} \quad (17)$$

$$Q_{k,x_n} = \begin{bmatrix} 0 & 0 \\ 0 & \sigma_{excavator}^2 \end{bmatrix} \quad (18)$$

The result is:

$$x_k^\# = \begin{bmatrix} m_{stockpile} - m_{excavator} \\ m_{excavator} \end{bmatrix}$$

$$P_k^\# = \begin{bmatrix} \sigma_{stockpile}^2 + \sigma_{excavator}^2 & -\sigma_{excavator}^2 \\ -\sigma_{excavator}^2 & \sigma_{excavator}^2 \end{bmatrix}$$

As seen from the results above the system behaves as expected. The mass in the stockpile is reduced by the mass in the excavator. The off-diagonal terms in A and B are equal in magnitude but opposite in sign to the excavator mass state. This fact will be used when fusing new information about the excavator mass state at a later time.

Removing lumped mass states and their correlations when the lumped mass is removed from the system or combined with another lumped mass ensures that the conservation of mass in the system is upheld. Practically it also reduces the complexity in the system (for example by reducing the covariance matrix size), enabling faster operation. Removing a lumped mass is performed when a system process removes all lumped material from a unique location and it is combined with another lumped mass (or initialized into a new lumped mass at a new location). Mathematically, the process involves removing the rows and columns associated with the lumped mass to be removed from the covariance matrix, and the necessary rows to be removed from the state matrix.

Sensor Models

Sensors used to observe material properties such as mass, volume and chemical composition are in most cases positively biased (i.e. not possible to be negative). This is particularly important when considering sensor observations which are made close to 0 with variances which extend probability density to areas less than zero.

In these circumstances the normal distribution is not an accurate representation of the sensor observation's probability density. This is a problem which arises commonly in mechanics and geographic surveys, when observations include random variables such as Spring Factors (K) and chemical mixture ratios. By their nature these values are non-negative.

Log-normal sensor models may be converted to normal distributions before Kalman filter operations in order to make the probability density more representative of the true distribution. A log-normal distribution only contains positive probability densities. See, for example, S. E. Cohn. Introduction to estimation theory. Journal of the Meteorological Society of Japan, 75:257-288, 1997.

Modelling Extensive Lumped Mass Properties

Extensive lumped mass properties include properties which define the amount of material present at the lumped mass location. These are the properties of mass and volume. Previously an example initialization was shown which involved modelling an extensive lumped mass property from a stockpile to an excavator. The modelling in that example can be generalized for any process with extensive lumped mass properties. The following equations show how correlations between a source location and subsequent locations may be maintained while maintaining a consistent estimate. Using the Kalman filter equations:

Variables:

$$x_k = \begin{bmatrix} \omega_1 \\ \omega_2 \end{bmatrix} \quad (21)$$

$$F = \begin{bmatrix} i & j \\ k & l \end{bmatrix} \quad (22)$$

$$Q_k = \begin{bmatrix} \sigma_1^2 & 0 \\ 0 & \sigma_2^2 \end{bmatrix} \quad (23)$$

Assume that $Q_k=0$.
Result:

$$x_{k+1} = \begin{bmatrix} i\omega_1 + j\omega_2 \\ k\omega_1 + l\omega_2 \end{bmatrix} \quad (24)$$

-continued $$P_{k+1} = \begin{bmatrix} i^2\sigma_{\omega_1}^2 + j^2\sigma_{\omega_2}^2 & lj\sigma_{\omega_2}^2 + ik\sigma_{\omega_1}^2 \\ lj\sigma_{\omega_2}^2 + ik\sigma_{\omega_1}^2 & l^2\sigma_{\omega_2}^2 + k^2\sigma_{\omega_1}^2 \end{bmatrix} \quad (25)$$

In order to constrain the problem to ensure conservation of mass, i and l are both set equal to one. This provides a fully correlated linear model. With this constraint the equations become:

$$x_{k+1} = \begin{bmatrix} \omega_1 + j\omega_2 \\ k\omega_1 + \omega_2 \end{bmatrix} \quad (26)$$

$$P_{k+1} = \begin{bmatrix} \sigma_{\omega_1}^2 + j^2\sigma_{\omega_2}^2 & j\sigma_{\omega_2}^2 + k\sigma_{\omega_1}^2 \\ j\sigma_{\omega_2}^2 + k\sigma_{\omega_1}^2 & \sigma_{\omega_2}^2 + k^2\sigma_{\omega_1}^2 \end{bmatrix} \quad (27)$$

This results shows that in all material transfer process cases (j,k=+1, 0, −1) the variance will linearly add to each state dependent on the system model. This is an important result when considering how to implement a mass loss model consistently.

Modelling Intensive Lumped mass Properties

Intensive lumped mass properties can be defined as properties which define the characteristics of the lumped material. For iron ore, this may involve properties such as chemical composition (Fe %, $SiO_2$%, $AlO_3$%, P %), density or fragmentation level.

To model these properties over material transfer processes raises several problems. Combining two lumped masses, each with a different intensive property mean and variance will result in a non-normal distribution. For example, if an excavator bucket contains a 40 t mass with an Fe content of 45% (variance 20%) and adds the 40 t to a haul truck which already contains 140 t of material with an Fe content of 60% (variance 20%), the resulting combination of the two lumped masses of material produces a non-Gaussian result. The divergence from a Gaussian distribution is related to the difference in means of the intensive states.

Another problem is that the mode of transfer will result in spatial dependence of the material properties within the lumped mass the material is transferred to.

The latter problem can be resolved within lumped masses of relative small quantity by assuming a uniform blending occurs. In iron ore mining this could be at lumped mass locations inside excavator buckets and haul trucks. Alternatively a spatial model may be developed for larger lumped masses, such as for stockpiles in mining. The following description assumes that uniform blending also occurs at the larger lumped masses.

Figure 9A:
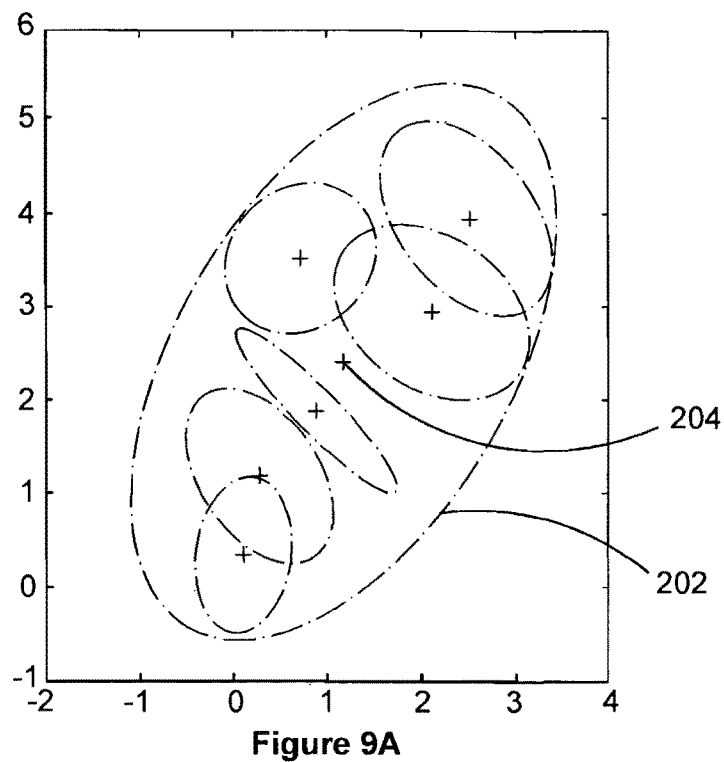
FIG. 9A shows a set of multiple Gaussian distributions.
Figure 9B:
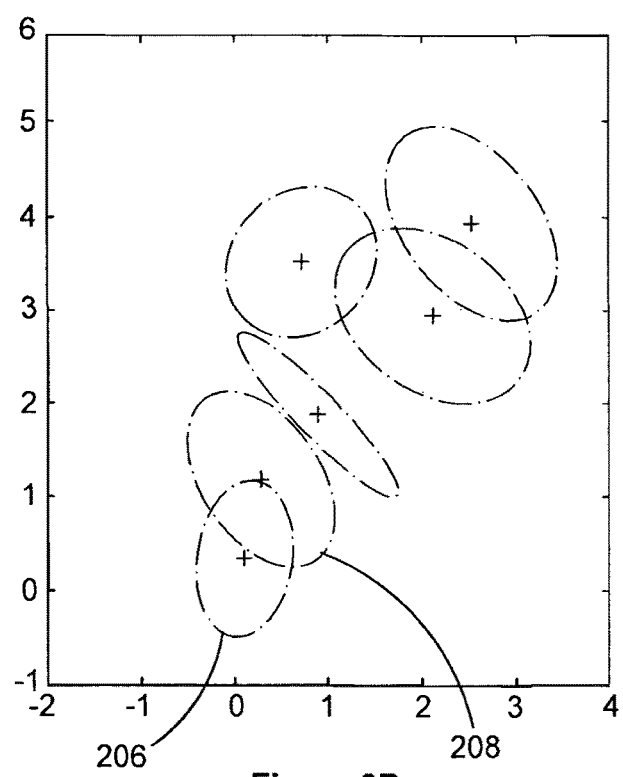
FIG. 9B illustrates a covariance union estimate superimposed on the distributions of FIG. 9A.

The non-normal distribution from the combination of lumped masses is a result of the disparity between the property means. A similar problem arises in Multiple Hypothesis Tracking (MHT) problems, such as tracking a vehicle through a city. Once the amount of hypotheses becomes too large it is necessary (due to computational reasons) to reduce the number of hypotheses to a more reasonable level. This can involve merging several hypotheses in a spatially similar area into a single estimate. One proposed method for solving this problem is the 'Covariance Union' method. This method finds a single most conservative estimate over a multitude of estimates, as illustrated in FIGS. 9A and 9B. FIG. 9B shows a distribution with a single mean 204 and variance 202 that represents the several different Gaussian distributions shown in FIG. 9A, for example Gaussian distributions 206 and 208. See, for example, Ottmar Bochardt, Ryan Calhoun, J. K. U. S. J. J. Generalized Information Representation and Compression Using Covariance Union 9th International Conference on Information Fusion, 2006.

Using this method on lumped mass data requires slight alterations from the base formulation. Using the basic formulation can result in outlying low mass results greatly altering the mean value of the property. With the alteration of using a weighted average based on the mass of each lumped mass, more reasonable results can be obtained.

Alternatively, given that it is known that the distribution is a sum of Gaussians rather than an arbitrary distribution, another approach is to determine from the initial formulation of the distribution the average mean and variance. This is referred to as the mathematical formulation method.

The average gaussian formula calculated from the sum of 2 Gaussians is shown in Equations 28 and 29.

$$x_J = \left(\frac{M_1}{M_1 + M_2}x_1\right) + \left(\frac{M_2}{M_1 + M_2}x_2\right) \quad (28)$$

$$\sigma_J^2 = \frac{M_1(\sigma_1^2 + x_1^2) + M_2(\sigma_2^2 + x_2^2)}{M_1 + M_2} - x_J^2 \quad (29)$$

Alternatively Equation 29 can also be written as:

$$\sigma_J^2 = \frac{M_1\sigma_1^2 + M_2\sigma_2^2}{M_1 + M_2} + \left(\frac{x_1 - x_2}{M_1 + M_2}\right)^2 M_1 M_2 \quad (30)$$

Where:
$x_J$=Combined Material Mean
$\sigma_J^2$=Combined Material Property Variance
$M_1$=Mass of Lumped mass 1
$M_2$=Mass of Lumped mass 2
$x_1$=Material Property 1 Mean
$x_2$=Material Property 2 Mean
$\sigma_1^2$=Material Property 1 Variance
$\sigma_2^2$=Material Property 2 Variance Equations 28 and 29 define a Gaussian distribution that has the same mean and variance as the sum of two Gaussians. The equations allow a simple and efficient method for approximating a weighted mean and variance when combining 2 lumped masses with intensive material properties. From Equation 30, it can be seen that the first term represents a weighted combination of the two previous lumped mass variances. The second term represents the additional variance required to compensate for the difference in mean values between the two lumped masses.

Determining which is the better method for variance approximation is a non-trivial task. The most ideal representation is one which most closely resembles the original probability distribution.

Figure 10:
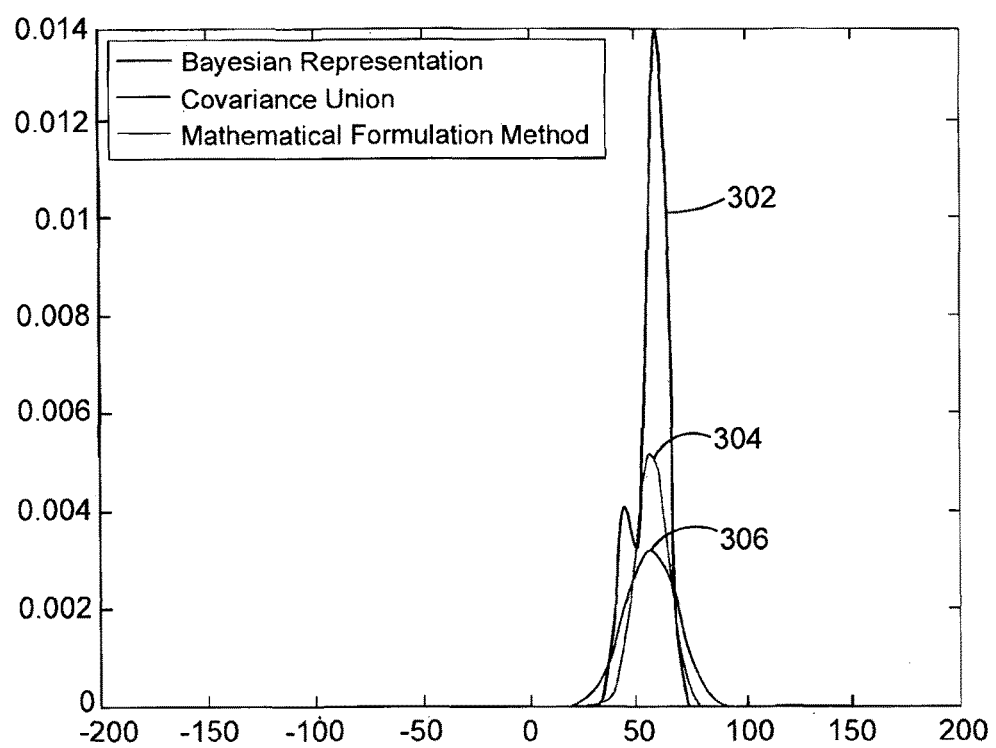
FIG. 10 illustrates a comparison of a covariance union approximation with an approximation based on a mathematical formulation.

FIG. 10 shows the original probability distribution 302 and the two previously described variance approximation technique estimates of this probability distribution (i.e. the covariance union 306 and mathematical formulation methods 304). Given that the shape and distribution of each of the approximation techniques are similar, it is not intuitive which technique better approximates the original distribution. The most obvious difference between the two techniques is the conservative nature of the covariance union method. This is to be expected given the nature of the covariance union where the most conservative estimate over the number of Gaussians is used to determine a single mean and variance.

One way of comparing these two techniques is to use a quantile-quantile (QQ) plot, which is a method for determining whether a different set of sampled data points comes from a known distribution. This method aims to determine which is the better fit for the original distribution.

Figure 11A:
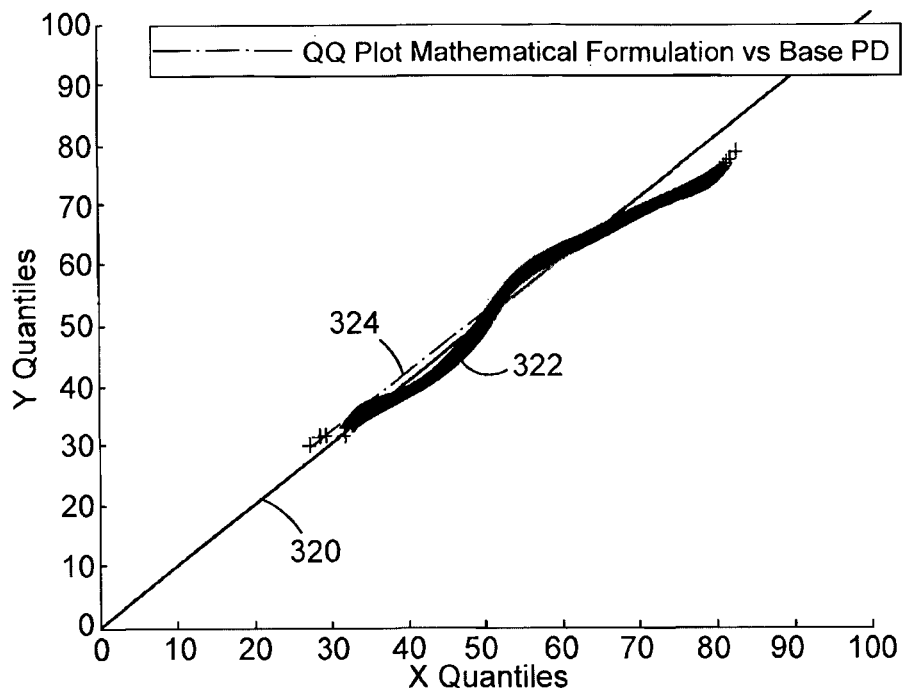
FIGS. 11A and 11B show a comparative assessment of the two approximation methods of FIG. 10 using a Q-Q plot.
Figure 11B:
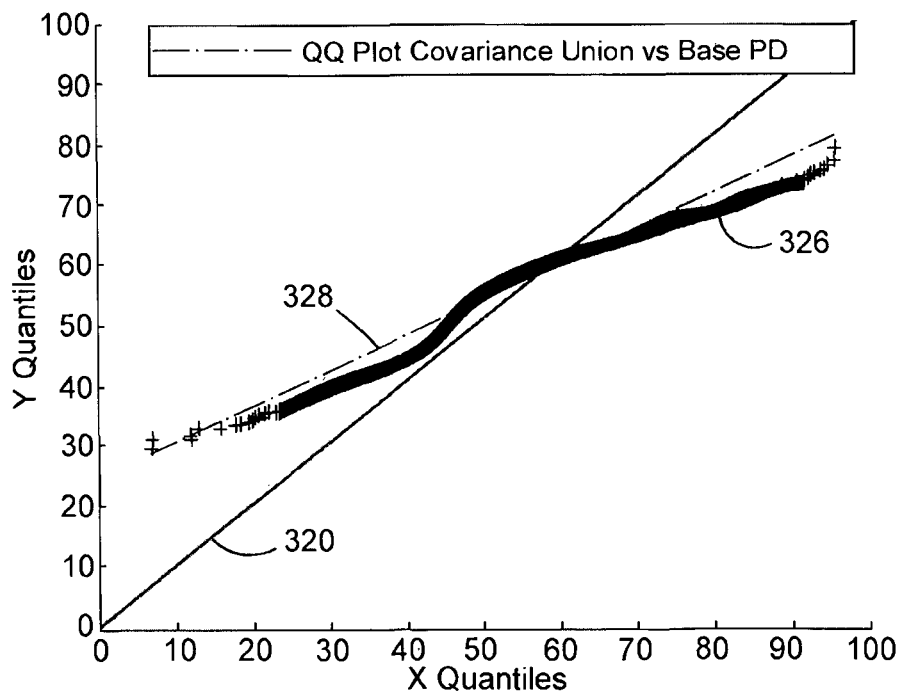

From the QQ plots shown in FIGS. 11A and 11B the mathematical formulation method is more representative of the original distribution. Ideally the sampled points should follow the 45 degree line 320 if the two distributions are the same. FIG. 11A compares the original distribution to the results 322 of the mathematical formulation. The dashed line 324 represents the linearity on average of the sampled data set 322. FIG. 11B compares the original distribution to the results 326 of the covariance union approach. The dashed line 328 represents the linearity on average of the sampled data set 326.

Another method for comparing distributions is by using the Kolmogov-Smirnov test. This is a test whereby the cumulative probability distributions of two sample sets are compared. If the sample sets are within a given tolerance limit the same, they are classified as the same. This test shows the maximum difference in probability density between the two sample sets.

Figure 12:
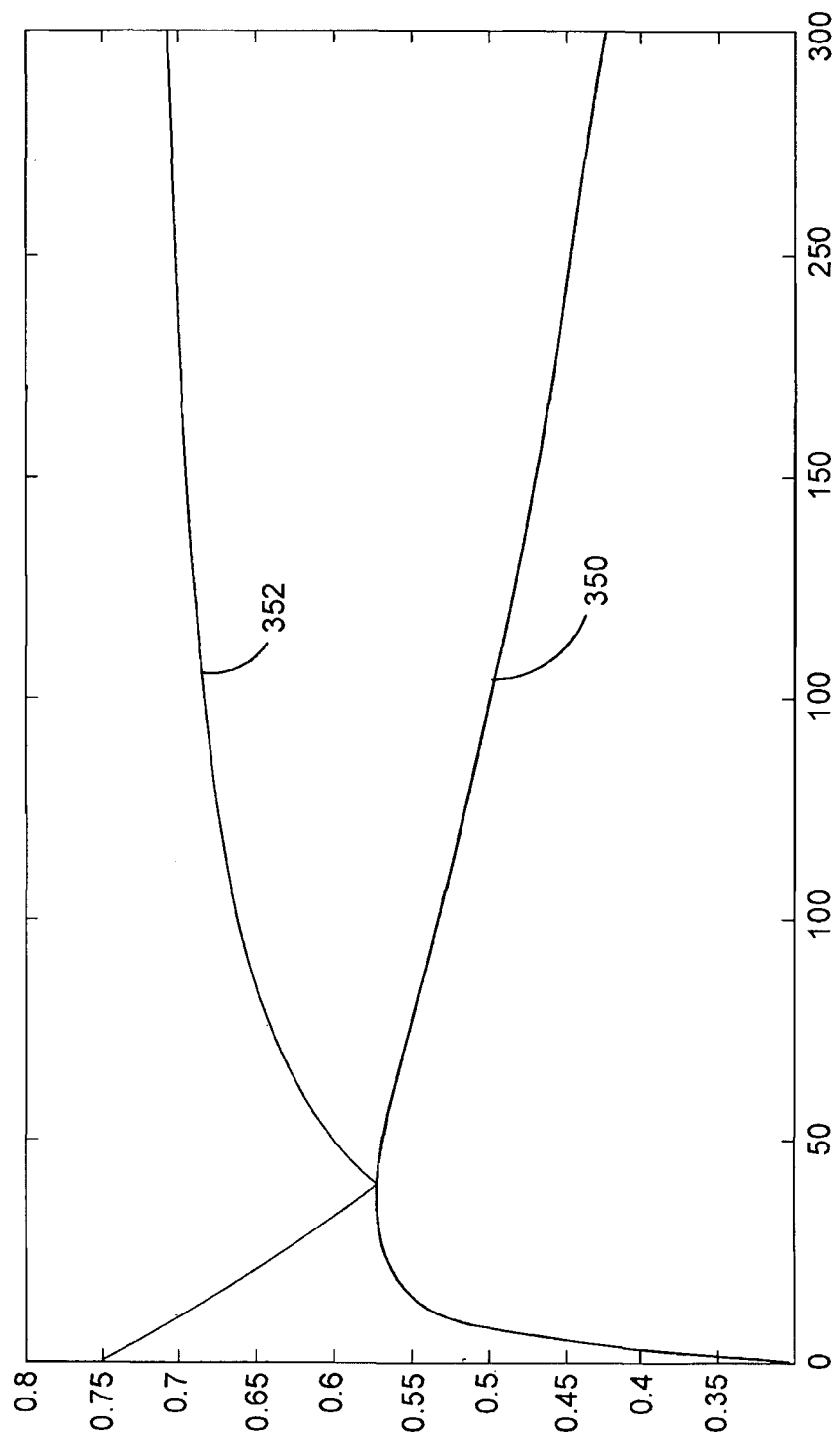
FIG. 12 shows a comparative assessment of the two approximation methods of FIG. 10 using a Kolmogorov-Smirnov test showing the maximum probability density difference over varying haul truck load sizes.

FIG. 12 shows the maximum difference in probability density given varied initial truck loads (x-axis). Curve 350 shows the difference between the original distribution and the mathematical formulation results. Curve 352 shows the difference between the original distribution and the covariance union results. The results show that on average, the mathematical formulation method gives a lower maximum error value in probability density compared to the covariance union method. This further emphasizes the benefit of using the mathematical formulation method over the covariance union method. However, other methods such as particle filters could also be used for estimating the intensive properties.

One advantage of the method described is that where information is available that estimates the chemical composition of the material at any point spatially, then the estimation of the chemical composition of each lumped mass of material may be tracked (and grouped as required) as it moves through the production process.

Mass Loss Modelling

Modelling and observing the mass loss in each process of the lumped mass system may be necessary. It is required to ensure that the estimates do not become positively or negatively biased. An example from mining arises when an excavator bucket is emptied into a waiting haul truck. Material may spill during movement, and thus the amount of material estimated and observed in a bucket does not neatly transition fully into the waiting haul truck. These system losses can be modelled in the same way as initializing a new lumped mass of material into the system shown in Equations 11-14.

The mass-loss lumped mass may be initialized as a subtraction from the estimate of material in the haul truck. This lumped mass may then be transferred back to the original block where the material was mined and removed. In mining, generally a dozer will push any loose material back into the area of excavation.

This helps prevent generally inaccurate loss models from inflating the variance on estimates.

Reconciliation and Conservation of Mass

An aim in bulk material tracking is to ensure that material is not 'invented'. Take again the simple example case of modelling an excavator loading material from a stockpile using two separate Kalman filters in a system similar to that shown in FIG. 8A, one filter for the stockpile and the other for the excavator bucket. When fusing new information about the material in excavator bucket, there is no automatic method to update the material in the stockpile to reflect the correlation between the two lumped materials. The excavator bucket can be carrying more or less material then what is estimated to be removed from the original stockpile. Thus after fusing in new information there may be a discrepancy of total mass in the system from what is originally estimated.

This problem can be overcome using the augmented state filter and general equations for mass transfer shown in Equations 21-25. The correlations developed in the system modelling act as natural constraint of mass in the system, preventing the 'invention' or unexplained disappearance of material. This can be proved by looking at the co-variance developed between a state and other states.

As an example, consider observing $\omega_2$ (From Equation 26).

$P_k H^T$ is used in calculating the Kalman gain. The term is a column vector containing the variance of the observed state and its co-variance to other states.

$$P_k H^T = \begin{bmatrix} j\sigma_{\omega_2}^2 + k\sigma_{\omega_1}^2 \\ \sigma_{\omega_2}^2 + k^2\sigma_{\omega_1}^2 \end{bmatrix} \quad (31)$$

Given that j and k must take one of the discrete values [−1,0,1], the relationships developed through the system models will remain linear since $k^2=0$ or 1. It is under these circumstances that the conservation of mass principle can be maintained. By extrapolating this to multiple states which develop over time, it is possible to harness this property for other uses such as probabilistic reconciliation.

Reconciliation in the mining industry is generally considered as the process of comparing the actual quality and amount of material mined from a designated area compared to the expected output of that area. It is useful as a tool to validate geological models and mine plans. Reconciliation is performed usually on monthly (or longer) schedules, which reduces the usefulness of the data for planning. A real-time reconciliation of extensive properties is possible using the framework discussed.

This can be achieved, for example, by adding a new special reconciliation state for a stockpile, initialized with 0 mean and variance. Material removed can be added to this state and conversely material added can be subtracted from the reconciliation state. This example can be shown in Equations 32-33.

$$x_{k+1} = \begin{bmatrix} m_{reconcile} \\ m_{excavator} \end{bmatrix} \quad (32)$$

$$F = \begin{bmatrix} 1 & 1 \\ 0 & 1 \end{bmatrix} \quad (33)$$

This will result in a state which in this example will track the net movement into and out of the designated stockpile. This approach could be applied to a mining grade block, and can determine the amount of material removed. By taking a mock observation of this state with estimated mean and 0 variance, the location and mean amount of material can be observed by viewing the correlations with mining grade block state.

By means of the correlations developed during this process, an algorithm may be developed which can reconcile material at later stages of the mining process back to the reconciled stage. The reconciliation may apply both to extensive properties such as mass and volume and to intensive properties such as chemical composition and fragmentation levels.

Reconciliation of Extensive Properties

The process of reconciling extensive properties is inherent in the described modelling method using an augmented state Kalman filter and the reconciliation states described above. The variances and covariances in the augmented state Kalman filter covariance matrix (P) may be used to isolate specific correlations. This can, for example, provide information on how much material in a particular stockpile has come from a specific grade block.

The following equations give an example of a state vector ($x_k$) and covariance matrix ($P_k$) of a hypothetical system filled with $M_n$ mass states.

$$x_k = \begin{bmatrix} M_1 \\ M_2 \\ \vdots \\ M_n \end{bmatrix}, P_k = \begin{bmatrix} \rho_{11} & \rho_{12} & \cdots & \rho_{1n} \\ \rho_{21} & \rho_{22} & \cdots & \rho_{2n} \\ \vdots & \vdots & \ddots & \\ \rho_{n1} & \rho_{n2} & & \rho_{nn} \end{bmatrix}$$

The amount of correlated mass from a particular state $M_a$ to a state $$M_b([M_a, M_b] \in x_k)$$

may be calculated as follows:

$$M_c = \alpha_{ab} \times M_a$$

where $$\alpha_{ab} = \frac{\rho_{ba}}{\rho_{aa}}$$

and $M_c$ is the total amount of correlated mass.

Reconciliation of Intensive Properties

The ability to calculate each correlation enables the reconciliation of intensive properties. Equations (28)-(30) describe how to combine two Gaussian distributed intensive properties into a single Gaussian for use in the augmented state Kalman filter. This mathematical formulation method may be applied iteratively to provide a reconciled estimate for the intensive property.

In the following equations $X_R$ defines an intensive property of the state which is to be reconciled and $\sigma_R^2$ provides the estimated variance of the reconciled state:

$$x_R = \frac{\alpha_{1R} M_1 x_1 + \alpha_{2R} M_2 x_2 + \ldots + \alpha_{nR} M_n x_n}{\alpha_{1R} M_1 + \alpha_{2R} M_2 + \ldots + \alpha_{nR} M_n} = \sum_{i=1}^{n} \frac{\alpha_{iR} M_i x_i}{\alpha_{iR} M_i}$$

$$\sigma_R^2 = \frac{\sum_{i=1}^{n} \alpha_{iR} M_i \sigma_i^2}{\sum_{i=1}^{n} \alpha_{iR} M_i} + \frac{\sum_{i<j, i, j=1}^{n} \alpha_{iR} M_i \alpha_{jR} M_j (x_i - x_j)^2}{\left(\sum_{i=1}^{n} \alpha_{iR} M_i\right)^2}$$

The reconciliation may be performed at specified intervals, for example once a day or once per shift. It may also be carried out when a specified event occurs. For example, a reconciliation may be performed if the state space is augmented or diminished. A reconciliation may also be performed if a new observation is available.

Example

Figure 13:
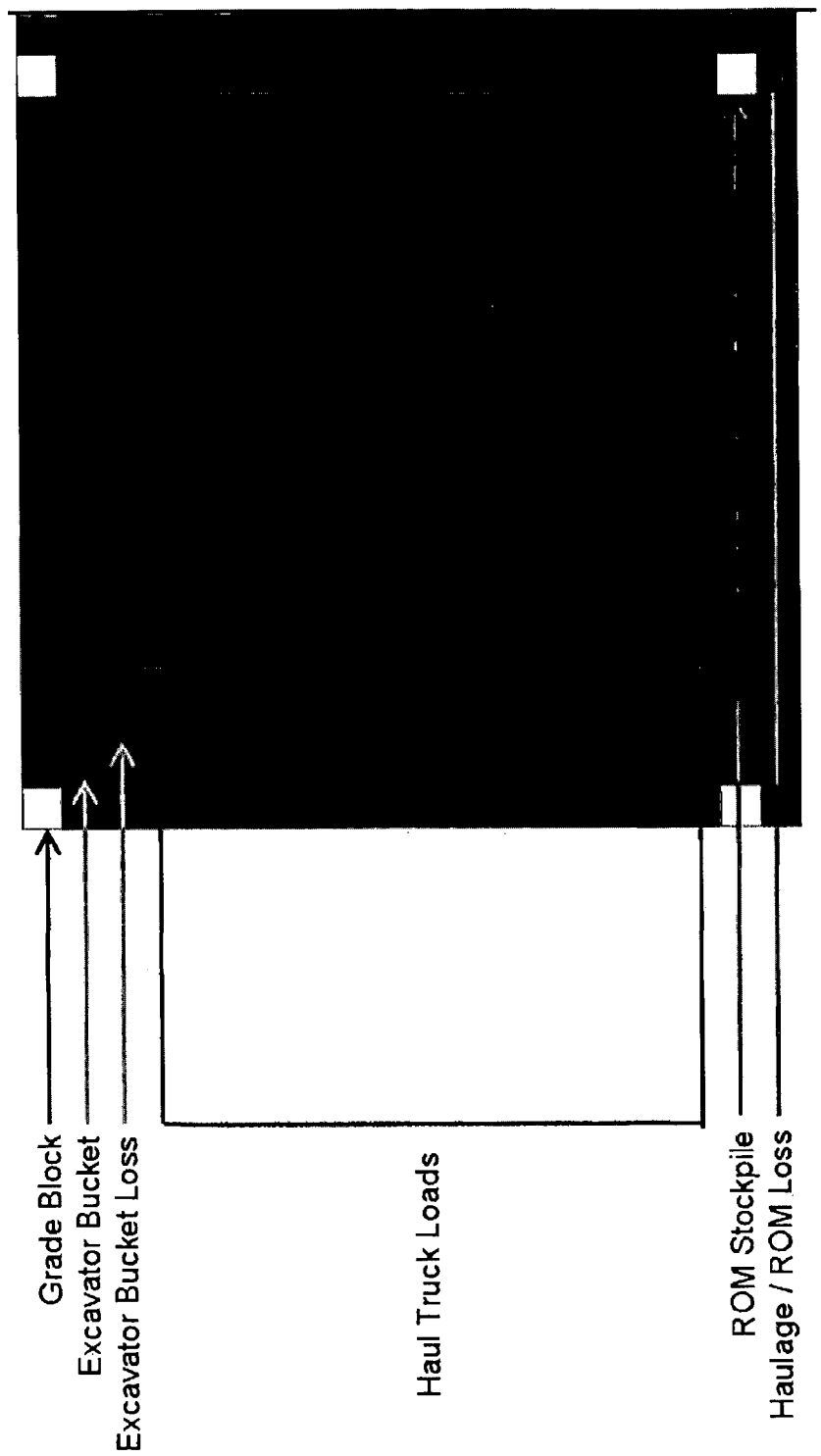
FIG. 13 shows a visual representation of a covariance matrix of an augmented-state Kalman filter for an open pit mining operation.

FIG. 13 shows a simple experimental example which involves estimating mass and volume from a simulated grade block to a ROM stockpile. FIG. 13 is a visual representation of the covariance matrix of the augmented state Kalman filter at the end of the experiment. The diagonal terms represent the progression from the grade block to the excavator bucket (and the associated state of excavator bucket loss), via several haul truck loads to the ROM stockpile. Black areas represent areas corresponding to 0. The lighter the colour, the higher the covariance value (white being the highest in this example). The values along the diagonal represent the variance of each state stored in the filter. The off diagonal terms represent the correlations between these states. The mass and volume states at each unique location are correlated through density. A key feature of the correlation map is the off-diagonal terms between material located at different locations. An example of this would be between the original grade block and the excavator bucket states. These correlations allow additional information gathered later in the production process to improve estimates of material located earlier in the production chain.

FIG. 14 gives a numerical example of how the process of fusing information at later stages improves estimates at earlier locations. When the excavator update occurs (fusion of new mass and volume data at that location), the amount of material estimated to be in the excavator bucket increases (ie bucket mass increases from 348 to 393). The variance on these estimates also decreases dramatically, which suggests the update was of high quality data. This update subsequently decreases the amount of material estimated to remain in the grade block (ie from 3994 to 3949) as well as improving the quality of this estimate. This effect propagates through the filter as the material is transferred from state to state.

Application to an Open Pit Mining Model

The tracking system can describe how material properties (e.g. mass, volume, chemical %) are transferred between unique locations (Grade Block, Excavator Bucket, Haul Truck etc). This application to an open pit mining model shows how the augmented state filter develops at the different production processes considered in the example.

The tracking methods may be used to track various properties or combinations of properties, including:
1. mass only;
2. volume only;
3. mass and volume;
4. one or more intensive properties of the material, in combination with mass estimates, volume estimates or estimates of both mass and volume.

1.1 Grade Block

The following section describes how the grade block property states are initialised into the augmented state filter system.

The filter prediction step equations are as follows:

$$x_{k+1} = F x_k$$

$$P_{k+1} = F P_k F' + G Q_k G' \quad (34) \text{ and } (35)$$

For initialisation of new states into the filter, initialisation matrices are used (from the filter prediction step equations the 'F' is substituted for an 'A' and G substitutes for B):

$$x_k = A x_k$$

$$P_k = A P_k A' + B Q_k B' \quad (36) \text{ and } (37)$$

These equations are used whenever a new state needs to be initialised.

$$x = \begin{bmatrix} Gradeblock \text{ Mass} \\ Gradeblock \text{ Volume} \\ Gradeblock \text{ Chemical Property} \end{bmatrix}$$

Where x is the current state vector ($x_k$).

In this example density $\rho$ is assumed to be known and to remain constant:

$$A = \begin{bmatrix} 1 & 0 & 0 \\ 0 & 1 & 0 \\ 0 & 0 & 1 \end{bmatrix}$$

$$B = \begin{bmatrix} 1 & \rho & 0 \\ \frac{1}{\rho} & 1 & 0 \\ 0 & 0 & 1 \end{bmatrix}$$

The matrix 'A' is an initialisation matrix which is applied to the state vector x. Appropriate variance estimates are assigned during the initialisation.

1.2 Grade Block—Excavator Bucket

Following the grade block initialisation, this section details the models describing the interaction between the excavator bucket and the grade block. Data fusion from sensor inputs is also included.

A grade-block-removed state is used in place of the actual grade block state described in the previous section. This state is used to store the current amount of material estimated to have been removed from the current grade block.

The excavator bucket state is initialised in a new state initialisation matrix.

$$x = \begin{bmatrix} Gradeblock \text{ Removed Mass} \\ Gradeblock \text{ Removed Volume} \\ \text{Bucket Mass} \\ \text{Bucket Volume} \\ \text{Bucket Chemical Property} \end{bmatrix}$$

For example, bucket mass and volume are initialised:

$$A = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix}$$

-continued $$B = \begin{bmatrix} 1 & 0 & 0 & 0 & 0 \\ 0 & 1 & 0 & 0 & 0 \\ 0 & 0 & 1 & \rho & 0 \\ 0 & 0 & \frac{1}{\rho} & 1 & 0 \\ 0 & 0 & 0 & 0 & 1 \end{bmatrix}$$

The following models use the filter prediction step equations to describe the process of removing material from the grade block. In this case, the material is added to the grade block removed states.

$$F = \begin{bmatrix} 1 & 0 & 1 & 0 & 0 \\ 0 & 1 & 0 & 1 & 0 \\ 0 & 0 & 1 & 0 & 0 \\ 0 & 0 & 0 & 1 & 0 \\ 0 & 0 & 0 & 0 & 1 \end{bmatrix}$$

The following state update equations are used to fuse the observed sensor input data for the excavator bucket into the filter:

$$v_{k+1} = z_{k+1} - Hx_{k+1}$$

$$S_{k+1} = HPH' + R$$

$$W_{k+1} = P_{k+1}H(S_{k+1})^{-1}$$

$$x_{+1}^+ = x_{k+1}^- + W_{k+1}v$$

$$P_{k+1}^+ = P_{k+1}^- - W_{k+1}S_{k+1}W'_{k+1}$$

Where:
z=State Observation Vector.
H=Describes how observation vector applies to state vector.
R=Sensor Noise
v=Innovation (Error between observed states and corresponding predicted states)
S=Innovation Covariance
W=Kalman Weighting
Excavator Bucket Observation Data Fusion:

$$H = \begin{bmatrix} 0 & 0 & 1 & 0 & 0 \\ 0 & 0 & 0 & 1 & 0 \\ 0 & 0 & 0 & 0 & 1 \end{bmatrix}$$

$$z_{k+1} = \begin{bmatrix} \text{Bucket Mass} \\ \text{Bucket Volume} \\ \text{Bucket Chemical Property} \end{bmatrix}$$

$$R = \begin{bmatrix} \sigma_{bms}^2 & 0 & 0 \\ 0 & \sigma_{bvs}^2 & 0 \\ 0 & 0 & \sigma_{bcs}^2 \end{bmatrix}$$

Where:
$\sigma_{bms}^2$=Excavator Bucket Sensor Mass Variance
$\sigma_{bvs}^2$=Excavator Bucket Sensor Volume Variance
$\sigma_{bcs}^2$=Excavator Bucket Sensor Chemical Variance 1.3 Excavator Bucket—Haul Truck This section details unloading the excavator bucket into a waiting haul truck.

The filter prediction step equations 34 and 35 are applied to transition material from the bucket to the haul truck. If the haul truck is not initialised yet in the filter, then the states are created with 0 mean and variance.

$$x = \begin{bmatrix} \text{Gradeblock Removed Mass} \\ \text{Gradeblock Removed Volume} \\ \text{Bucket Mass Loss} \\ \text{Bucket Volume Loss} \\ \text{Bucket Mass} \\ \text{Bucket Volume} \\ \text{Bucket Chemical Property} \\ \text{Haul Truck Mass} \\ \text{Haul Truck Volume} \\ \text{Haul Truck Chemical Property} \end{bmatrix}$$

On the first load all properties from the excavator bucket are transferred to the empty haul truck:

$$F = \begin{bmatrix} 1 & 0 & 0 & 0 & 0 & 0 & 0 & 0 & 0 & 0 \\ 0 & 1 & 0 & 0 & 0 & 0 & 0 & 0 & 0 & 0 \\ 0 & 0 & 1 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 0 & 0 & 0 & 0 & 0 & 0 \\ 0 & 0 & 0 & 0 & 0 & 0 & 0 & 0 & 0 & 0 \\ 0 & 0 & 0 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 1 & 0 & 0 & 0 & 0 & 0 \\ 0 & 0 & 0 & 0 & 0 & 1 & 0 & 0 & 0 & 0 \end{bmatrix}$$

On subsequent loads where there is material already present in the haul truck, the mean and variance approximation equations 28 and 29 may be used to alter the intensive (chemical %) properties in the state vector and covariance matrix for the haul truck:

The matrix below describes the effect of these equations on the state-transition-matrix.

$$F = \begin{bmatrix} 1 & 0 & 0 & 0 & 0 & 0 & 0 & 0 & 0 & 0 \\ 0 & 1 & 0 & 0 & 0 & 0 & 0 & 0 & 0 & 0 \\ 0 & 0 & 1 & 0 & 0 & 0 & 0 & 0 & 0 & 0 \\ 0 & 0 & 0 & 1 & 0 & 0 & 0 & 0 & 0 & 0 \\ 0 & 0 & 0 & 0 & 0 & 0 & 0 & 0 & 0 & 0 \\ 0 & 0 & 0 & 0 & 0 & 0 & 0 & 0 & 0 & 0 \\ 0 & 0 & 0 & 0 & 0 & 0 & 0 & 0 & 0 & 0 \\ 0 & 0 & 0 & 0 & 1 & 0 & 0 & 1 & 0 & 0 \\ 0 & 0 & 0 & 0 & 0 & 1 & 0 & 0 & 1 & 0 \\ 0 & 0 & 0 & 0 & 0 & 0 & 0 & 0 & 0 & \eta \end{bmatrix}$$

Where
$\eta$=Scalar to multiply original base property after combining lumped masses.

The state update equations are used to fuse the observed haul truck observation information into the filter as follows:

$$H = \begin{bmatrix} 0 & 0 & 0 & 0 & 0 & 0 & 1 & 0 & 0 \\ 0 & 0 & 0 & 0 & 0 & 0 & 0 & 1 & 0 \\ 0 & 0 & 0 & 0 & 0 & 0 & 0 & 0 & 1 \end{bmatrix}$$

$$z = \begin{bmatrix} \text{Haul Truck Mass} \\ \text{Haul Truck Volume} \\ \text{Haul Truck Chemical Property} \end{bmatrix}$$

$$R = \begin{bmatrix} \sigma_{hms}^2 & 0 & 0 \\ 0 & \sigma_{hvs}^2 & 0 \\ 0 & 0 & \sigma_{hcs}^2 \end{bmatrix}$$

Where:
$\sigma_{hms}^2$ = Haul Truck Sensor Mass Variance
$\sigma_{hvs}^2$ = Haul Truck Sensor Volume Variance
$\sigma_{hcs}^2$ = Haul Truck Sensor Chemical Variance In this scenario, the material from the excavator bucket is intended to be wholly transferred to the haul truck. However, this is not always the case and there are inevitably some unintended material transfers or losses. Losses from the excavator bucket to the haul truck are calculated in this example once the haul truck is full. To ensure that the correct correlations are maintained, a temporary loss state is used to transfer the estimated lost material.

$$A = \begin{bmatrix} 1 & 0 & 0 & 0 & 0 & 0 & 0 & 0 & 0 \\ 0 & 1 & 0 & 0 & 0 & 0 & 0 & 0 & 0 \\ 0 & 0 & 1 & 0 & 0 & 0 & 0 & 0 & 0 \\ 0 & 0 & 0 & 1 & 0 & 0 & 0 & 0 & 0 \\ 0 & 0 & 0 & 0 & 1 & 0 & 0 & 0 & 0 \\ 0 & 0 & 0 & 0 & 0 & 1 & 0 & 0 & 0 \\ 0 & 0 & 0 & 0 & 0 & 0 & 1 & 0 & 0 \\ 0 & 0 & 0 & 0 & 0 & 0 & 0 & 1 & 0 \\ 0 & 0 & 0 & 0 & 0 & 0 & 0 & 1 & 0 \\ 0 & 0 & 0 & 0 & 0 & 0 & 0 & 0 & 1 \end{bmatrix}$$

Once the loss state is initialised with the expected losses and the variance associated with these losses it is applied to the current system model. In this particular example it is assumed the material lost from the bucket will be fully returned to the original grade block, thus subtracting from the estimated material removed.

$$F = \begin{bmatrix} 1 & 0 & -1 & 0 & 0 & 0 & 0 & 0 & 0 \\ 0 & 1 & 0 & -1 & 0 & 0 & 0 & 0 & 0 \\ 0 & 0 & 1 & 0 & 0 & 0 & 0 & 0 & 0 \\ 0 & 0 & 0 & 1 & 0 & 0 & 0 & 0 & 0 \\ 0 & 0 & 0 & 0 & 1 & 0 & 0 & 0 & 0 \\ 0 & 0 & 0 & 0 & 0 & 1 & 0 & 0 & 0 \\ 0 & 0 & 0 & 0 & 0 & 0 & 1 & 0 & 0 \\ 0 & 0 & -1 & 0 & 0 & 0 & 1 & 0 & 0 \\ 0 & 0 & 0 & -1 & 0 & 0 & 0 & 1 & 0 \\ 0 & 0 & 0 & 0 & 0 & 0 & 0 & 0 & 1 \end{bmatrix}$$

1.4 Haul Truck—Run of Mine (ROM) Stockpile

The final system process is the unloading from the haul truck to the ROM stockpile. The models used in this process are described below. This process is nearly identical in theory to the Excavator Bucket—Haul Truck scenario. There are a few minor alterations however with the loss modelling.

$$x = \begin{bmatrix} \textit{Gradeblock} \text{ Removed Mass} \\ \textit{Gradeblock} \text{ Removed Volume} \\ \text{Bucket Mass Loss} \\ \text{Bucket Volume Loss} \\ \text{Bucket Mass} \\ \text{Bucket Volume} \\ \text{Bucket Chemical Property} \\ \text{Haul 1 Truck Mass} \\ \text{Haul 1 Truck Volume} \\ \text{Haul 1 Truck Chemical Property} \\ \vdots \\ \vdots \\ \text{Haul } k \text{ Truck Mass} \\ \text{Haul } k \text{ Truck Volume} \\ \text{Haul Truck Chemical Property} \\ \textit{ROM} \text{ Stockpile Mass} \\ \textit{ROM} \text{ Stockpile Volume} \\ \textit{ROM} \text{ Stockpile Chemical Property} \end{bmatrix}$$

On first load only all the haul truck state properties are fully transferred to the new ROM Stockpile $$F = \begin{bmatrix} 1 & 0 & 0 & 0 & 0 & 0 & 0 & 0 & 0 & \cdots & 0 & 0 & 0 & 0 & 0 & 0 \\ 0 & 1 & 0 & 0 & 0 & 0 & 0 & 0 & 0 & \cdots & 0 & 0 & 0 & 0 & 0 & 0 \\ 0 & 0 & 1 & 0 & 0 & 0 & 0 & 0 & 0 & \cdots & 0 & 0 & 0 & 0 & 0 & 0 \\ 0 & 0 & 0 & 1 & 0 & 0 & 0 & 0 & 0 & \cdots & 0 & 0 & 0 & 0 & 0 & 0 \\ 0 & 0 & 0 & 0 & 1 & 0 & 0 & 0 & 0 & \cdots & 0 & 0 & 0 & 0 & 0 & 0 \\ 0 & 0 & 0 & 0 & 0 & 1 & 0 & 0 & 0 & \cdots & 0 & 0 & 0 & 0 & 0 & 0 \\ 0 & 0 & 0 & 0 & 0 & 0 & 1 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ \vdots & \vdots & \vdots & \vdots & \vdots & \vdots & \vdots & \vdots & \vdots & \ddots & \vdots & \vdots & \vdots & \vdots & \vdots & \vdots \\ 0 & 0 & 0 & 0 & 0 & 0 & 0 & 0 & 0 & \cdots & 1 & 0 & 0 & 0 & 0 & 0 \\ 0 & 0 & 0 & 0 & 0 & 0 & 0 & 0 & 0 & \cdots & 0 & 1 & 0 & 0 & 0 & 0 \\ 0 & 0 & 0 & 0 & 0 & 0 & 0 & 0 & 0 & \cdots & 0 & 0 & 1 & 0 & 0 & 0 \\ 0 & 0 & 0 & 0 & 0 & 0 & 1 & 0 & 0 & \cdots & 0 & 0 & 0 & 1 & 0 & 0 \\ 0 & 0 & 0 & 0 & 0 & 0 & 0 & 1 & 0 & \cdots & 0 & 0 & 0 & 0 & 1 & 0 \\ 0 & 0 & 0 & 0 & 0 & 0 & 0 & 0 & 1 & \cdots & 0 & 0 & 0 & 0 & 0 & 1 \end{bmatrix}$$

On subsequent loads variance and weighted mean approximations are used for intensive properties.

$$F = \begin{bmatrix} 1 & 0 & 0 & 0 & 0 & 0 & 0 & 0 & 0 & \cdots & 0 & 0 & 0 & 0 & 0 & 0 \\ 0 & 1 & 0 & 0 & 0 & 0 & 0 & 0 & 0 & \cdots & 0 & 0 & 0 & 0 & 0 & 0 \\ 0 & 0 & 1 & 0 & 0 & 0 & 0 & 0 & 0 & \cdots & 0 & 0 & 0 & 0 & 0 & 0 \\ 0 & 0 & 0 & 1 & 0 & 0 & 0 & 0 & 0 & \cdots & 0 & 0 & 0 & 0 & 0 & 0 \\ 0 & 0 & 0 & 0 & 1 & 0 & 0 & 0 & 0 & \cdots & 0 & 0 & 0 & 0 & 0 & 0 \\ 0 & 0 & 0 & 0 & 0 & 1 & 0 & 0 & 0 & \cdots & 0 & 0 & 0 & 0 & 0 & 0 \\ 0 & 0 & 0 & 0 & 0 & 0 & 1 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ 0 & 0 & 0 & 0 & 0 & 0 & 0 & 0 & 0 & \cdots & 0 & 0 & 0 & 0 & 0 & 0 \\ \vdots & \vdots & \vdots & \vdots & \vdots & \vdots & \vdots & \vdots & \vdots & \ddots & \vdots & \vdots & \vdots & \vdots & \vdots & \vdots \\ 0 & 0 & 0 & 0 & 0 & 0 & 0 & 0 & 0 & \cdots & 1 & 0 & 0 & 0 & 0 & 0 \\ 0 & 0 & 0 & 0 & 0 & 0 & 0 & 0 & 0 & \cdots & 0 & 1 & 0 & 0 & 0 & 0 \\ 0 & 0 & 0 & 0 & 0 & 0 & 0 & 0 & 0 & \cdots & 0 & 0 & 1 & 0 & 0 & 0 \\ 0 & 0 & 0 & 0 & 0 & 0 & 1 & 0 & 0 & \cdots & 0 & 0 & 0 & 1 & 0 & 0 \\ 0 & 0 & 0 & 0 & 0 & 0 & 0 & 1 & 0 & \cdots & 0 & 0 & 0 & 0 & 1 & 0 \\ 0 & 0 & 0 & 0 & 0 & 0 & 0 & 0 & 0 & \cdots & 0 & 0 & 0 & 0 & 0 & \eta \end{bmatrix}$$

Where
η=Scalar to multiply original base property after combining lumped masses.

The state vector becomes:

$$x = \begin{bmatrix} \text{Gradeblock Removed Mass} \\ \text{Gradeblock Removed Volume} \\ \text{Bucket Mass Loss} \\ \text{Bucket Volume Loss} \\ \text{Bucket Mass} \\ \text{Bucket Volume} \\ \text{Bucket Chemical Property} \\ \text{Haul 1 Truck Mass} \\ \text{Haul 1 Truck Volume} \\ \text{Haul 1 Truck Chemical Property} \\ \vdots \\ \vdots \\ \text{Haul } k \text{ Truck Mass} \\ \text{Haul } k \text{ Truck Volume} \\ \text{Haul} k \text{ Truck Chemical Property} \\ ROM \text{ Stockpile Mass} \\ ROM \text{ Stockpile Volume} \\ ROM \text{ Stockpile Chemical Property} \\ ROM \text{ Stockpile Mass Loss} \\ ROM \text{ Stockpile Volume Loss} \end{bmatrix}$$

Loss modelling on haul trucks is very similar to modelling on the excavator buckets. The main exception is that it is assumed that no material which is lost from the haul truck will be recovered. Thus, there is a constantly increasing haul truck loss state which develops.

$$F = \begin{bmatrix} 1 & 0 & 0 & 0 & 0 & 0 & 0 & 0 & 0 & \cdots & 0 & 0 & 0 & 0 & 0 & 0 & 0 & 0 \\ 0 & 1 & 0 & 0 & 0 & 0 & 0 & 0 & 0 & \cdots & 0 & 0 & 0 & 0 & 0 & 0 & 0 & 0 \\ 0 & 0 & 1 & 0 & 0 & 0 & 0 & 0 & 0 & \cdots & 0 & 0 & 0 & 0 & 0 & 0 & 0 & 0 \\ 0 & 0 & 0 & 1 & 0 & 0 & 0 & 0 & 0 & \cdots & 0 & 0 & 0 & 0 & 0 & 0 & 0 & 0 \\ 0 & 0 & 0 & 0 & 1 & 0 & 0 & 0 & 0 & \cdots & 0 & 0 & 0 & 0 & 0 & 0 & 0 & 0 \\ 0 & 0 & 0 & 0 & 0 & 1 & 0 & 0 & 0 & \cdots & 0 & 0 & 0 & 0 & 0 & 0 & 0 & 0 \\ 0 & 0 & 0 & 0 & 0 & 0 & 1 & 0 & 0 & \cdots & 0 & 0 & 0 & 0 & 0 & 0 & 0 & 0 \\ 0 & 0 & 0 & 0 & 0 & 0 & 0 & 1 & 0 & \cdots & 0 & 0 & 0 & 0 & 0 & 0 & -1 & 0 \\ 0 & 0 & 0 & 0 & 0 & 0 & 0 & 0 & 1 & \cdots & 0 & 0 & 0 & 0 & 0 & 0 & 0 & -1 \\ 0 & 0 & 0 & 0 & 0 & 0 & 0 & 0 & 1 & \cdots & 0 & 0 & 0 & 0 & 0 & 0 & 0 & 0 \\ \vdots & \vdots & \vdots & \vdots & \vdots & \vdots & \vdots & \vdots & \vdots & \ddots & \vdots & \vdots & \vdots & \vdots & \vdots & \vdots & \vdots & \vdots \\ 0 & 0 & 0 & 0 & 0 & 0 & 0 & 0 & 0 & \cdots & 1 & 0 & 0 & 0 & 0 & 0 & 0 & 0 \\ 0 & 0 & 0 & 0 & 0 & 0 & 0 & 0 & 0 & \cdots & 0 & 1 & 0 & 0 & 0 & 0 & 0 & 0 \\ 0 & 0 & 0 & 0 & 0 & 0 & 0 & 0 & 0 & \cdots & 0 & 0 & 1 & 0 & 0 & 0 & 0 & 0 \\ 0 & 0 & 0 & 0 & 0 & 0 & 0 & 0 & 0 & \cdots & 0 & 0 & 0 & 1 & 0 & 0 & 0 & 0 \\ 0 & 0 & 0 & 0 & 0 & 0 & 0 & 0 & 0 & \cdots & 0 & 0 & 0 & 0 & 1 & 0 & 0 & 0 \\ 0 & 0 & 0 & 0 & 0 & 0 & 0 & 0 & 0 & \cdots & 0 & 0 & 0 & 0 & 0 & 1 & 0 & 0 \\ 0 & 0 & 0 & 0 & 0 & 0 & 0 & 0 & 0 & \cdots & 0 & 0 & 0 & 0 & 0 & 0 & 1 & 0 \\ 0 & 0 & 0 & 0 & 0 & 0 & 0 & 0 & 0 & \cdots & 0 & 0 & 0 & 0 & 0 & 0 & 0 & 1 \end{bmatrix}$$

In this example the methods do not use observation data from the final ROM stockpiles to update estimates.

The percentage make up of each ROM stockpile from the different source grade blocks can be achieved by observing the correlations developed in the covariance matrix, thus blending ratio estimates can be updated in real-time.

A probabilistic framework for describing excavated material properties in lumped masses has been developed. This probabilistic framework was implemented using an augmented state Kalman filter. This framework has been developed to deal with spatially separated material in a process based system. This involves developing appropriate loss modelling techniques for materials, appropriate mean and variance models for different material properties, development of an appropriate framework to facilitate reconciliation as well as constraints such as conservation of mass in the system. A method for autonomous estimation of bulk volume for flat based surfaces is also developed to aid implementation into an autonomous environment.

One advantage of the method described is that where there is an in-ground model that estimates the chemical composition of the material at any point spatially then the estimation of the chemical composition of each lumped mass of material may be tracked (and grouped as required) as it moves through the production process.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A method for a tracking system to track material through a production chain or operational process chain in which the material is transferred via a plurality of spatially distinct lumped masses of material, the method comprising:
   measuring, with a plurality of sensors, attributes of the spatially distinct lumped masses of material;
   maintaining a dynamic state space descriptive of an estimate of material in the plurality of spatially distinct lumped masses of material, wherein a quantity of entries in the dynamic state space is varied dependent on a quantity of spatially distinct lumped masses being tracked;
   maintaining a dynamic covariance matrix associated with the dynamic state space, wherein a dimension of the dynamic covariance matrix is varied dependent on a quantity of spatially distinct lumped masses of material being tracked;
   receiving one or more measurements from the plurality of sensors relating to an observed lumped mass of material;
   fusing the received one or more measurements into the dynamic state space and dynamic covariance matrix to provide an update of an estimate of material in the plurality of spatially distinct lumped masses of material; and
   updating the tracking system with the update of the estimate of material as the plurality of spatially distinct lumped masses of material move through the production chain or operational process chain.

2. The method of claim 1 wherein each entry in the dynamic state space comprises one or more values descriptive of a corresponding spatially distinct lumped mass of material.

3. The method of claim 2 wherein the one or more values descriptive of a spatially distinct lumped mass of material comprise an extensive lumped mass property defining an amount of material present in the spatially distinct lumped mass.

4. The method of claim 3 wherein the extensive lumped mass property comprises at least one of lumped-mass volume and lumped-mass mass.

5. The method of claim 2 wherein the one or more values descriptive of a spatially distinct lumped mass of material comprise an intensive lumped mass property defining a characteristic of the material present in the spatially distinct lumped mass.

6. The method of claim 5 wherein the intensive lumped mass property comprises at least one of a chemical composition, density and a fragmentation level.

7. The method of claim 5 further comprising:
determining a combined mean and a combined variance for an intensive lumped mass property of a combined lumped mass if a first lumped mass is combined with a second lumped mass.

8. The method of claim 7 wherein determining the combined mean and variance comprises finding a covariance union that includes the means and variances or the first and second lumped masses.

9. The method of claim 8 wherein finding the covariance union comprises the use of weighted averages dependent on a mass of the first lumped mass and a mass of the second lumped mass.

10. The method of claim 7 wherein the intensive lumped mass property of the first lumped mass of material and the second lumped mass of material are treated as Gaussian distributions and wherein determining the combined mean and combined variance comprises calculating an average Gaussian distribution from a sum of the Gaussian distributions of the first and second lumped masses of material.

11. The method of claim 1 wherein maintaining the dynamic state space comprises augmenting the state space by adding an additional entry corresponding to an additional spatially distinct lumped mass.

12. The method of claim 1 wherein maintaining the dynamic state space comprises removing an entry from the dynamic state space if a corresponding spatially distinct lumped mass of material is removed from the tracked production chain.

13. The method of claim 1 wherein maintaining the dynamic state space comprises removing an entry from the dynamic state space if a corresponding lumped mass of material is combined with another one of the plurality of lumped masses of material.

14. The method of claim 1 wherein maintaining the dynamic covariance matrix comprises augmenting the covariance matrix by adding additional rows and columns corresponding to an additional spatially distinct lumped mass of material.

15. The method of claim 1 wherein maintaining the dynamic covariance matrix comprises removing rows and columns from the covariance matrix that correspond to a spatially distinct lumped mass of material that is removed from the tracked production chain or combined with another spatially distinct lumped mass of material.

16. The method of claim 1 comprising:
estimating a material loss that occurs when material is transferred from a first spatially distinct lumped mass of material to a second spatially distinct lumped mass of material.

17. The method of claim 16 comprising:
augmenting the dynamic state space to include a new entry descriptive of the material loss.

18. The method of claim 1 comprising:
receiving data from a scan of a surface of material in a spatially distinct lumped mass;
applying a Gaussian Process to the received data to estimate a volume of material in the spatially distinct lumped mass.

19. The method of claim 18 comprising estimating the volume by approximating a triple integral of a set of resultant points estimated by the Gaussian Process.

20. The method of claim 1 comprising:
applying a Kalman filter to fuse the received measurements into the dynamic state space and dynamic covariance matrix.

21. The method of claim 1 wherein the production chain is an open pit mine and the spatially distinct lumped masses of material are selected from the group consisting of:
a grade-block lumped mass comprising material in a grade block;
an excavator-bucket lumped mass comprising material in an excavator bucket;
an excavator-bucket-loss lumped mass comprising material spilt during transfer from an excavator bucket to a haul truck;
a haul-truck lumped mass comprising material loaded into a haul truck;
a stockpile lumped mass comprising material in a stockpile; and
a haulage lumped mass comprising material removed from a stockpile.

22. The method of claim 1 wherein the plurality of spatially distinct lumped masses of material define a sequence through the production chain and wherein observations on an observed lumped mass in the sequence are used to improve an estimate of material in another lumped mass that is earlier in the sequence.

23. The method of claim 1 further comprising determining, based on the dynamic state space and the dynamic covariance matrix, how much mass in a first specified lumped mass of material derives from a second specified lumped mass.

24. A system for tracking material through a mining production chain in which the material is transferred via a plurality of spatially distinct lumped masses of material, the system comprising:
a plurality of sensors for measuring attributes of the spatially distinct lumped masses of material; and
a processor in data communication with the plurality of sensors and comprising instructions that, in use, cause the processor to:
maintain a dynamic state space descriptive of an estimate of material in the plurality of spatially distinct lumped masses, wherein a quantity of entries in the dynamic state space is varied dependent on a quantity of spatially distinct lumped masses of material being tracked;
receive one or more measurements from the plurality of sensors relating to an observed lumped mass of material; and
fuse the received one or more measurements into the dynamic state space to provide an update of the estimate of material in the plurality of spatially distinct lumped masses of material; and
update the system with the update of the estimate of material as the plurality of spatially distinct lumped masses of material move through the mining production chain.

25. The system of claim 24 wherein the plurality of sensors includes at least one of:
a mass sensor arrangement that provides a measure of a mass of a spatially distinct lumped mass of material;
a volume sensor arrangement that provides a measure of a volume of a spatially distinct lumped mass of material;

a location sensor arrangement that provides a measure of a location of a spatially distinct lumped mass of material;

a grade sensor arrangement that provides a measure of a composition of a spatially distinct lump of material.

26. The system of claim 25 wherein the mass or volume sensor arrangement comprises:

a scanner that, in use, scans a surface of an observed lumped mass of material and outputs scan data; and a processor that receives the scan data and estimates a volume or mass in the observed lumped mass of material.

27. The system of claim 26 wherein the scanner comprises at least one of a radar, a laser and a camera.

28. The system of claim 24 wherein at least one sensor is mounted on a vehicle.

29. The system of claim 24 comprising:

a data source having an estimated in-ground model describing a composition of material that in use is excavated in the mining production chain.

30. The system of claim 24 wherein the estimate of material comprises an estimate of masses of the spatially distinct lumped masses of material in the mining production chain.

31. The system of claim 24 wherein the estimate of material comprises an estimate of volumes of the spatially distinct lumped masses of material in the mining production chain.

32. The system of claim 30 wherein the estimate of material further comprises an estimate of at least one intensive property of the spatially distinct lumped masses of material in the mining production chain.

33. The system of claim 24 wherein each entry in the dynamic state space comprises one or more values descriptive of a corresponding spatially distinct lumped mass of material.

34. The system of claim 24 wherein maintaining the dynamic state space comprises augmenting the state space by adding an additional entry corresponding to an additional spatially distinct lumped mass.

35. The system of claim 24 wherein maintaining the dynamic state space comprises removing an entry from the dynamic state space if a corresponding spatially distinct lumped mass of material is removed from the tracked production chain.

36. The system of claim 24 wherein maintaining the dynamic state space comprises removing an entry from the dynamic state space if a corresponding lumped mass of material is combined with another one of the plurality of lumped masses of material.

37. A system for tracking material through a mining production chain, comprising:

a) at least one excavator having:
  i) an excavator sensor that in use scans a surface of material to be excavated; and
  ii) a location sensor,
  wherein, based on the surface scan, an associated processor estimates a quantity of material excavated by the excavator as a first spatially distinct lumped mass of material;

b) at least one haul truck that in use receives excavated material from the at least one excavator, wherein material loaded into the haul truck comprises a second spatially distinct lumped mass of material and wherein, in use, material is offloaded from the at least one haul truck to define at least a third spatially distinct lumped mass of material;

c) a monitoring system that tracks movement of the at least one haul truck; and d) a material-tracking processor in data communication with the at least one excavator, the at least one haul truck and the monitoring system, wherein the material tracking processor maintains a dynamic state space descriptive of the first, second and third spatially distinct lumped masses of material and fuses information characterising the material in the mining production chain to provide an updated estimate of the spatially distinct lumped masses of material.

* * * * *